US010449322B2

(12) United States Patent
Poormand

(10) Patent No.: US 10,449,322 B2
(45) Date of Patent: Oct. 22, 2019

(54) SYSTEMS AND METHODS FOR HEATING AND HUMIDIFYING INSPIRED GASES DURING MECHANICAL VENTILATION

(71) Applicant: Flexicare, Inc., Irvine, CA (US)

(72) Inventor: Ghassem Poormand, London (GB)

(73) Assignee: Flexicare, Inc., Irvine, CA (US)

( * ) Notice: Subject to any disclaimer, the term of this patent is extended or adjusted under 35 U.S.C. 154(b) by 787 days.

(21) Appl. No.: 14/962,980

(22) Filed: Dec. 8, 2015

(65) Prior Publication Data

US 2016/0256659 A1 Sep. 8, 2016

Related U.S. Application Data

(60) Provisional application No. 62/089,481, filed on Dec. 9, 2014.

(51) Int. Cl.
| | | |
|---|---|---|
| A61M 16/16 | (2006.01) |
| A61M 16/04 | (2006.01) |
| A61M 16/06 | (2006.01) |
| A61M 16/08 | (2006.01) |
| A61M 16/10 | (2006.01) |
| A61M 16/00 | (2006.01) |

(52) U.S. Cl.
CPC ........ *A61M 16/16* (2013.01); *A61M 16/0051* (2013.01); *A61M 16/0461* (2013.01); *A61M 16/0465* (2013.01); *A61M 16/0488* (2013.01); *A61M 16/0666* (2013.01); *A61M 16/0875* (2013.01); *A61M 16/109* (2014.02); *A61M 16/1095* (2014.02); *A61M 16/161* (2014.02); *A61M 2205/3368* (2013.01); *A61M 2205/502* (2013.01); *A61M 2205/505* (2013.01)

(58) Field of Classification Search
CPC .. A61M 16/00; A61M 16/022; A61M 16/024; A61M 16/0051; A61M 16/0875; A61M 16/1075; A61M 16/1085; A61M 16/109; A61M 16/1095; A61M 16/16; A61M 16/161; A61M 2205/3368; A61M 2205/502; A61M 2205/505
See application file for complete search history.

(56) References Cited

U.S. PATENT DOCUMENTS

| | | |
|---|---|---|
| 4,621,632 A | 11/1986 | Bartels et al. |
| 5,857,062 A | 1/1999 | Bergamaschi et al. |
| 6,078,730 A | 6/2000 | Huddart et al. |
| 6,272,933 B1 | 8/2001 | Gradon et al. |

(Continued)

FOREIGN PATENT DOCUMENTS

| | | |
|---|---|---|
| EP | 2471568 A2 | 7/2012 |
| WO | WO 2013/137753 A1 | 9/2013 |

(Continued)

OTHER PUBLICATIONS

PCT International Search Report dated Feb. 25, 2016 in related PCT Application No. PCT/US2015/064528.

(Continued)

*Primary Examiner* — Joseph D. Boecker
(74) *Attorney, Agent, or Firm* — Robert D. Buyan; Stout, Uxa & Buyan, LLP

(57) ABSTRACT

Systems and methods for heating and/or humidifying a respiratory gas or gas mixture delivered to a human or animal patient during spontaneous or mechanical ventilation.

18 Claims, 40 Drawing Sheets

(56) References Cited

U.S. PATENT DOCUMENTS

| | | | |
|---|---|---|---|
| 6,584,972 B2 | 7/2003 | McPhee | |
| 6,694,974 B1 | 2/2004 | Gradon et al. | |
| 6,802,314 B2 | 10/2004 | McPhee | |
| 6,895,803 B2 | 5/2005 | Seakins et al. | |
| 7,043,979 B2 | 5/2006 | Smith et al. | |
| 7,051,733 B2 | 5/2006 | Gradon et al. | |
| 7,106,955 B2 | 9/2006 | Thudor et al. | |
| 7,111,624 B2 | 9/2006 | Thudor et al. | |
| 7,146,979 B2 | 12/2006 | Seakins et al. | |
| 7,263,994 B2 | 9/2007 | Gradon et al. | |
| 7,306,205 B2 | 12/2007 | Huddart et al. | |
| 7,383,839 B2 | 6/2008 | Porat et al. | |
| 7,428,902 B2 | 9/2008 | Du et al. | |
| RE40,806 E | 6/2009 | Gradon et al. | |
| 7,588,029 B2 | 9/2009 | Smith et al. | |
| 7,962,018 B2 | 6/2011 | Hunt et al. | |
| 8,091,547 B2 | 1/2012 | Thudor et al. | |
| 8,245,710 B2 | 8/2012 | Makinson et al. | |
| 8,616,202 B2 | 12/2013 | Tatkov et al. | |
| 2002/0100320 A1* | 8/2002 | Smith | A61M 16/1075 73/431 |
| 2004/0079370 A1 | 4/2004 | Gradon et al. | |
| 2007/0284361 A1 | 12/2007 | Nadjafizadeh et al. | |
| 2009/0024008 A1* | 1/2009 | Brunner | A61M 16/0051 600/301 |
| 2009/0223514 A1* | 9/2009 | Smith | A61M 16/1075 128/203.14 |
| 2011/0088693 A1 | 4/2011 | Somervell et al. | |
| 2011/0164002 A1 | 7/2011 | Hill et al. | |
| 2012/0185792 A1* | 7/2012 | Kimm | A61B 5/085 715/772 |
| 2014/0034056 A1* | 2/2014 | Leone | A61M 16/0051 128/204.23 |
| 2015/0048530 A1* | 2/2015 | Cheung | A61M 16/16 261/129 |
| 2015/0107588 A1* | 4/2015 | Cheung | A61M 16/16 128/203.14 |
| 2015/0217079 A1* | 8/2015 | Mcauley | A61M 16/109 128/203.14 |
| 2015/0343167 A1* | 12/2015 | Rybicki | A61M 16/06 128/203.14 |
| 2016/0256642 A1* | 9/2016 | Soysa | A61M 16/00 |
| 2017/0266408 A1* | 9/2017 | Giovannelli | G06F 19/00 |

FOREIGN PATENT DOCUMENTS

| | | |
|---|---|---|
| WO | WO2013/151448 A2 | 10/2013 |
| WO | WO 2013/165263 A1 | 11/2013 |
| WO | WO 2014/052983 A1 | 4/2014 |

OTHER PUBLICATIONS

Extended European Search Report dated Sep. 13, 2018 in related European Application No. 15867699.9.

* cited by examiner

SYSTEMS AND METHODS FOR HEATING AND HUMIDIFYING INSPIRED GASES DURING MECHANICAL VENTILATION

RELATED APPLICATION

This patent application claims priority to U.S. Provisional Patent Application Ser. No. 62/089,481 filed Dec. 9, 2014, the entire disclosure of which is expressly incorporated herein by reference.

FIELD OF THE INVENTION

The present invention relates generally to the fields of medicine and biomedical engineering and more particularly to systems and methods used for heating and humidifying inspired gases delivered to a human or animal patient.

BACKGROUND

During normal breathing, mucous membranes which line the upper airway heat and humidify the inspired air so that it is at or near body temperature (37 degrees C.) with about 100% relative humidity when it enters the lungs. However, when a patient is undergoing mechanical ventilation, the inspiratory gases may be delivered through an invasive artificial airway device (such as an endotracheal tube or tracheostomy tube) such that they bypass much of the mucosal tissue of the upper airway, or sometimes through non-invasive airway devices, such as those used to deliver Continuous Positive Airway Pressure (CPAP) and high flow therapies. Because inspired gases delivered from mechanical ventilators or flow generators can be relatively cold and dry, it is typically desirable to heat and humidify the inspired gases before they enter the lungs. Insufficient humidification of the inspired gases can lead to clinically significant loss of body heat and water, with resultant inspissation of airway secretions, hypothermia and impaired pulmonary gas exchange due to alveolar atelectasis. In patients receiving respiratory therapy through mechanical ventilation or flow generators, heating and humidification of the inspired gases is usually accomplished by either a heat and moisture exchanger (HME) or a heater/humidifier (HH). With either of these systems, it is generally desirable to ensure that the inspired gas contains at least about 30 mg of water for each liter of inspired gas delivered at 33+2° C. Generally, HME's are used only for short periods of time (less than 24 hours), such as during transport of an intubated patient or during postoperative anesthesia recovery.

HH's are typically used when longer term mechanical ventilation is required or when use of an HME is contraindicated. HME's are passive humidification systems wherein a hygroscopic filter (e.g., hygroscopic foam or paper material that may be treated with salts) positioned at the out end of the artificial airway retains heat and moisture as the patient exhales. On the next inspiratory cycle, the dry and cold inspired gases from the ventilator are heated and humidified by the heat and moisture retained in the HME from previously exhaled breaths. HH's are active humidification and heating systems in which heat and vapor generating apparatus are used to add controlled amounts of heat and humidity to inspired gases as they are delivered to the patient. Cold and dry inspired gases from the ventilator pass through a humidification apparatus where water vapor (and some heat) is added to the inspired gases. In some cases, a heated wire is placed in the inspiratory conduit to maintain the temperature of the inspired gases and to minimize water condensation as the inspired gases are delivered to the patient airway.

An important aspect of any modern HH system is the precision with which a user may control the operation of the humidifying and heating apparatus and monitor the temperature and humidity of inspired gases at critical locations in the respiratory circuit. One commercially available HH system is the MR850 Respiratory Humidifier (Fisher & Paykel Healthcare, Auckland, New Zealand). This system compromises a humidifier that has a heater and a water chamber and a control panel, a heating wire positioned in the inspiratory conduit of the ventilation circuit and temperature sensors for monitoring temperature at the humidifier and at the patient airway end of the inspiratory conduit. The control panel includes a digital temperature display capable of displaying only one temperature at a time and several control buttons (e.g., a power on/off button, mode button and mute button) which the user must know how to manipulate in specific ways in order to bring about specific desired outcomes.

Other examples of HH systems and/or components thereof are described in U.S. Pat. No. 4,621,632 (Bartels, et al.) entitled Humidifier System; U.S. Pat. No. 5,857,062 (Bergamaschi, et al.) entitled Heated Respiratory Therapy Humidifier, U.S. Pat. No. 7,106,955 (Thudor, et al.) entitled Humidity Controller; U.S. Pat. No. 7,428,902 (Du, et al.) entitled Humidifier System for Artificial Respiration; U.S. Pat. No. 7,962,018 (Hunt, et al.) entitled Humidity Controller; U.S. Pat. No. 8,616,202 (Tatkov, et al.) entitled Control of Humidifier Chamber Temperature for Accurate Humidity Control, the entire disclosure of each such patent being expressly incorporated herein by reference.

There exists a need in the art for the development of new HH systems having enhanced control and monitoring capabilities for improved patient ventilation, safety and ease of use.

SUMMARY OF THE INVENTION

In general, the present invention provides systems for delivering respiratory gas to a patient. The system generally includes a humidifier which has a chamber, a heating element and an outlet; an inspiratory conduit having a chamber end connectable to the outlet of the humidifier and a patient end connectable to a patient airway apparatus; a heating member extending through or along at least a substantial portion of the inspiratory conduit; at least one airway sensor located at a patient airway sensor location at or near the patient end of the inspiratory conduit, said airway sensor being operative to sense the temperature and/or humidity of respiratory gas at or near the patient end of the inspiratory conduit; at least chamber end sensor located at a chamber sensor location and operative to sense temperature and/or humidity of respiratory gas at or near the chamber of the humidifier and a controller having a user interface. The user interface, which may be a touch screen display, may be operative to allow a user to either accept default temperature and humidity setting and/or to input manual temperature and/or humidity settings to the controller within a clinically desired range. The controller is programmed to then control the amount of humidity delivered by the humidifier and/or the amount of heat delivered by the heating member based on the default or manually input settings.

BRIEF DESCRIPTION OF THE DRAWINGS

As non-limiting examples of the present invention, this patent application includes the following figures.

DETAILED DESCRIPTION OF EXAMPLES

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

The accompanying drawings show examples of interactive and non-interactive content displayed on a touch screen type user interface of an H&H system of the present invention.

Figure 1:
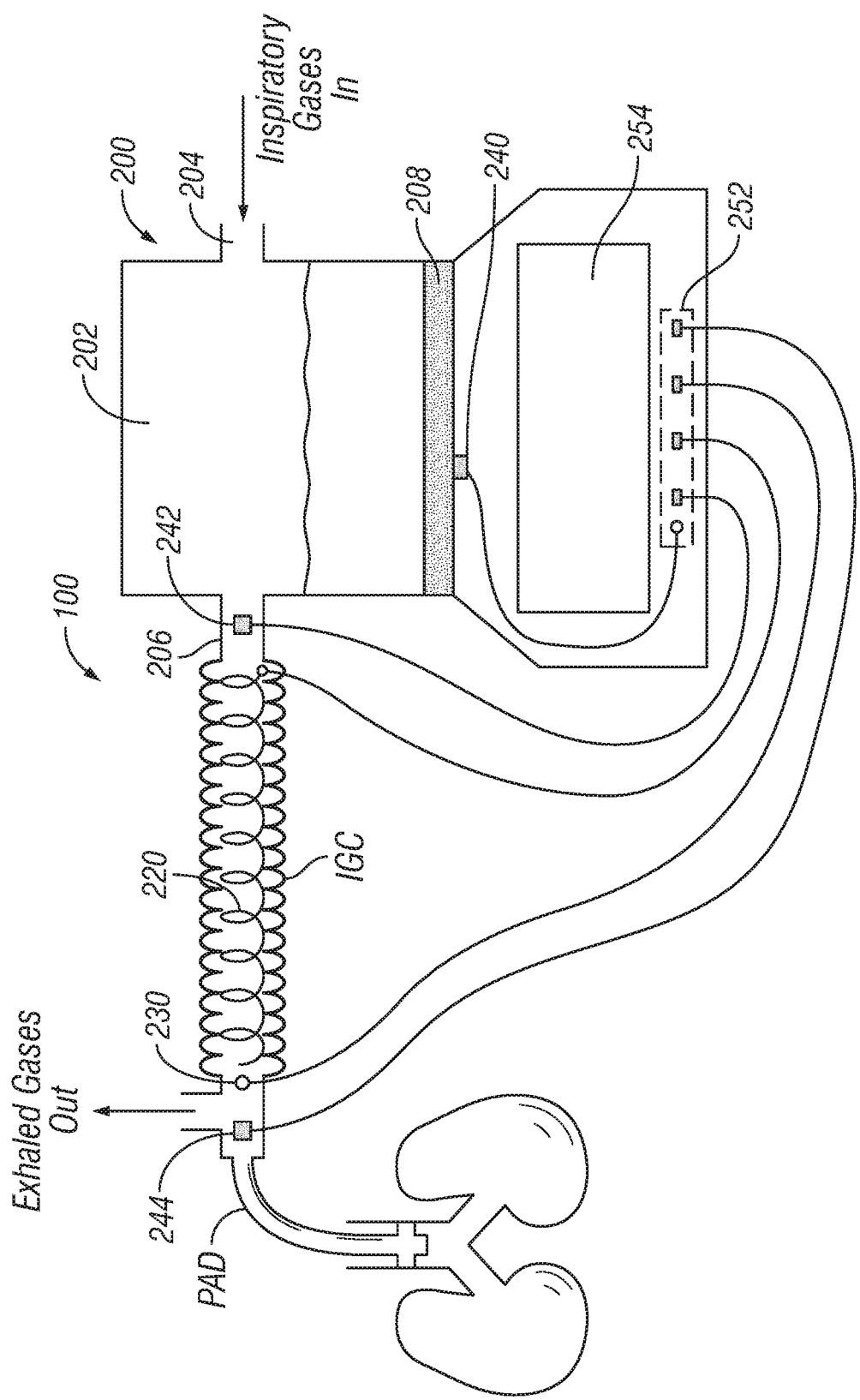
FIG. 1 is a diagram of one embodiment of a heating/humidifying system of the present invention.

As shown in FIG. 1, basic components of an H&H system 100 of the present invention may include a humidifier device 200, an inspiratory gas heating element 220, at least one humidity sensor 230 (e.g., Dickson TM325 High Accuracy Remote Probe Temperature & Humidity Logger), at least first, second and third temperature sensors 240, 242 and 244 (e.g., Dickson TM325 High Accuracy Remote Probe Temperature & Humidity Logger or Dickson SM425 High Accuracy Temperature Logger with Platinum RTD Probe) and a controller/user interface 250 as described below.

The humidifier device 200 typically comprises a chamber 202 which has an inlet 204 and an outlet 206 and a humidifier heating element 208 (e.g., a heated plate) which heats liquid that has been placed in the chamber 202.

In typical operation, the inspiratory gas heating element 220 is positioned in or on an inspiratory gas conduit IGC. One end of the inspiratory gas conduit EGO is connected to the outlet 206 of the humidifier chamber 202. The other end of the inspiratory gas conduit ISG is connected to a patient airway device PAD. The patient airway device PAD can be any type of non-invasive or invasive device for delivering inspiratory gases to a patient. Examples of non-invasive patient airway devices include face masks[1], nasal masks, nasal cannulae, nasal plugs, breathing tents, etc. Examples of invasive patient airway devices include all manner of insertable or indwelling breathing conduits such as endotreacheal tubes, endobroncheal tubes, nasotracheal tubes, tracheostomy tubes, supraglottic airways (SGA), laryngeal mask airways (LMA), mouthpieces, etc.

[1] The term "face mask" as used herein includes basic face masks which fit loosely over the patient's mouth and nose as well as more specialized, tightly-fitting face masks used for delivery of certain modes of assisted ventilation such as continuous positive airway pressure (CPAP) and bi-level positive airway pressure (BiPAP).

A quantity of desired liquid, such as sterile water, is placed in the chamber 202. The inlet 204 of the chamber 202 is connected to a source of inspiratory gas, which may simply be a source of compressed room air or oxygen-enriched room air or ventilation device, such as a mechanical ventilator, CPAP machine, BiPAP machine, anesthesia machine, etc.

As the humidifier heating element 208 heats the liquid within the chamber 202, the liquid vaporizes. The vapor then mixes with (i.e., humidifies) inspiratory gases which enter the chamber 202 through inlet 204. Humidified inspiratory gases then exit the chamber 202 through outlet 206 and travel through the inspiratory gas conduit EGO to the patient airway device PAD and into the patient's lungs. The inspiratory gas heating element 220 may be used to maintain or control the temperature of the humidified inspiratory gases as they travel through the inspiratory gas conduit IGC.

The first temperature sensor 240 may be positioned so as to sense the temperature of the humidifier heating element 208 (e.g., the surface temperature of a heated plate at the base of the humidifier chamber). The second temperature sensor 242 may be positioned to sense the temperature of humidified inspiratory gases exiting the chamber 202 or within the inspiratory gas conduit IGC at or near its connection to the chamber outlet 206. The third temperature sensor 244 may be positioned within the inspiratory gas conduit IGC at or near its connection to the patient airway device PAD.

The humidity sensor 230 may be positioned within the inspiratory gas conduit IGC at or near its connection to the patient airway device PAD. Optionally, additional humidity sensor(s) may be positioned at one or more additional locations in the inspiratory gas conduit IGC or chamber 202.

The controller/user interface 250 may comprise a programmable microprocessor 252 of a type generally known in the an (e.g. Intel Corporation, Mountain View, Calif.; Advanced Micro Devices, Inc., Sunnyvale, Calif.) connected to or having touch screen type user interface 254 of a type generally known in the art (e.g., Palm Technology Co., Ltd., Kaohsiung City Taiwan, R.O.C.). As described in more detail below, the controller 252 is in wired or wireless communication with, and receives data signals from, the humidity sensor(s) 230 and temperature sensors 240, 242 and 244. The controller 252 also receives settings or other information that is input by a user via the user interface 254. The controller 252 is in wired or wireless communication with at least the humidifier heating element 208 and inspiratory gas heating element 220 and is programmed to control the temperature of the humidifier heating element 208 and inspiratory gas heating element 220 in response to settings and/or other information input by the user and feedback from the humidity sensor(s) 230 and/or temperature sensors 240, 242 and 244.

Figure 2:
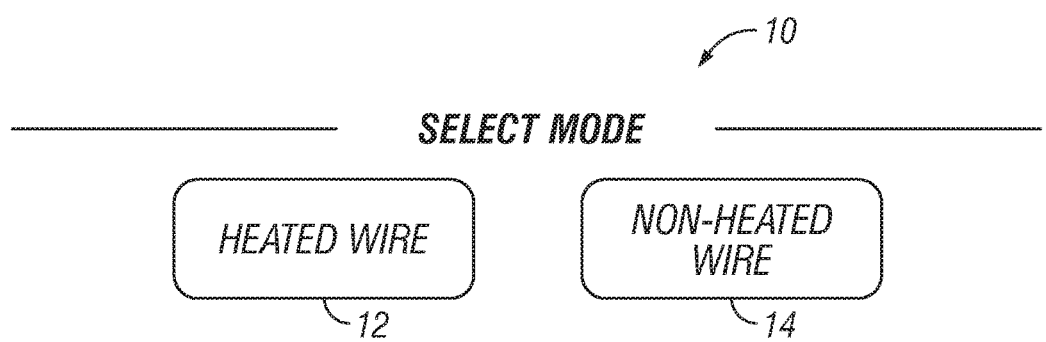
FIGS. 2 through 2C are examples of some of the mode selection screens that may appear on a touch screen user interface of a system of the present invention whereby a user may elect to operate the system in either HEATED MODE or NON-HEATED and either INVASIVE or NON-INVASIVE mode.
Figure 2A:
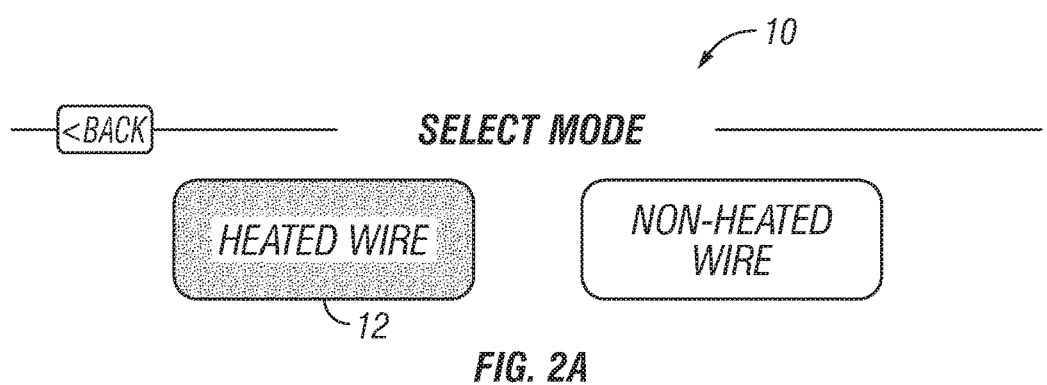
Figure 2B:
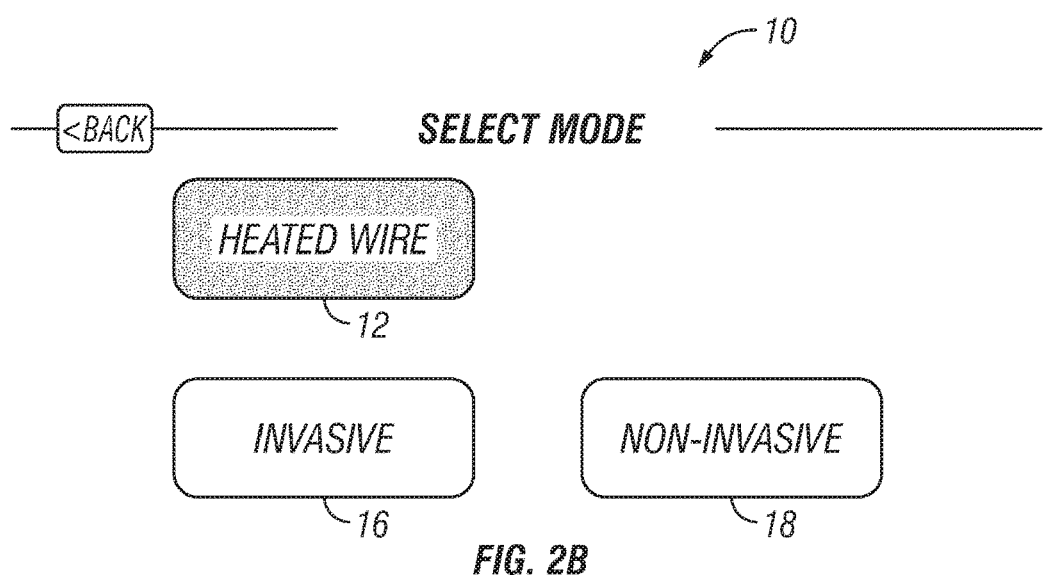
Figure 2C:
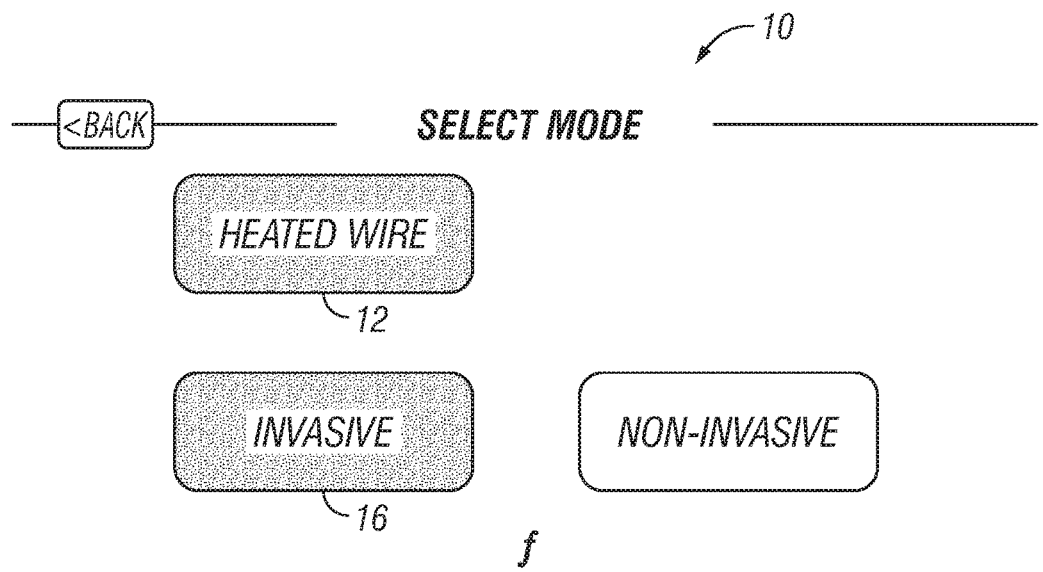

FIGS. 2 through 2C are examples of some of the mode selection screens that may appear on a touch screen user interface 254 of the H&H system 100. As seen in FIG. 2, the user is initially presented with a "Select Mode" screen whereby the user may touch selection icons for either heated wire 12 or non-heated wire 14. Whichever icon 12, 14 is pressed by the user will illuminate and will signal the controller 252 to operate in either heated mode or non-heated mode. FIG. 2A shows, for example, the manner in which the touch screen will appear immediately after the user has selected and pressed the "heated wire" icon 12. Thereafter, as seen in FIG. 2B, additional touch screen icons will appear to allow the user to select either invasive 16 or non-invasive 18. The invasive mode icon 16 will be selected and will become illuminated if the patient airway device PAD is of an invasive type and the non-invasive icon 18 will be selected and will become illuminated if the patient airway device PAD is of a non-invasive type. FIG. 2C shows, for example, the manner in which the touch screen will appear immediately after a user has selected and pressed the heated wire icon 12 and invasive airway icon 16. This signals the controller to operate in these selected modes.

Figure 3:
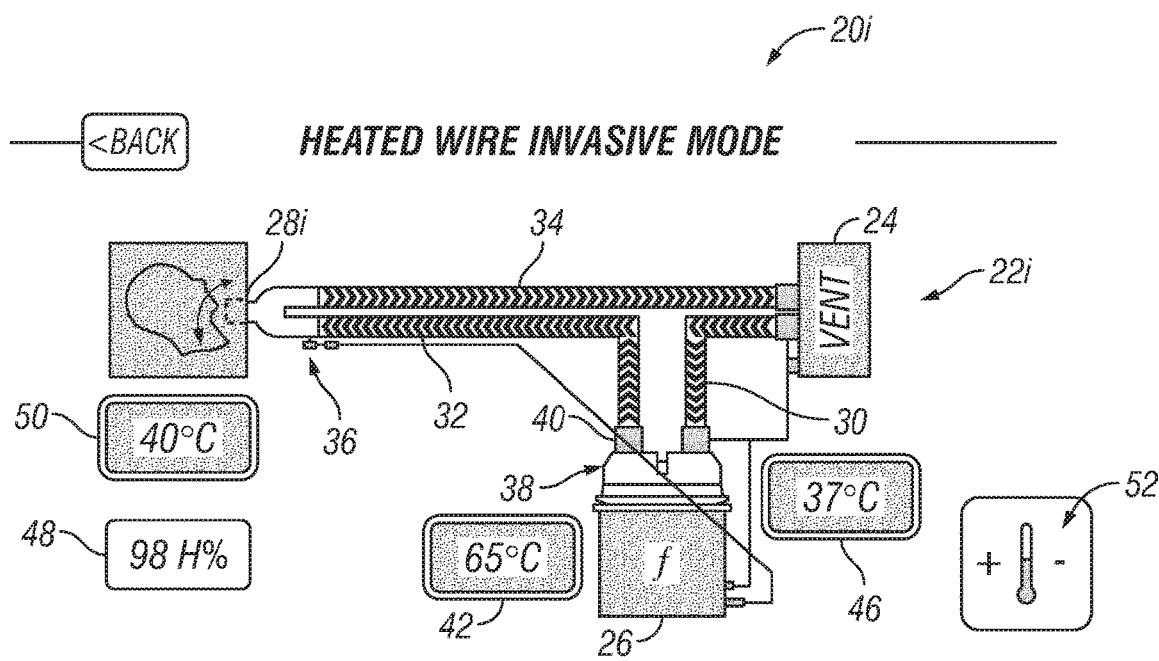
FIGS. 3 through 3F are examples of some of the operational screens that may appear on a touch screen user interface of a system of the present invention after a user has selected to operate the system in HEATED/INVASIVE mode.
Figure 3A:
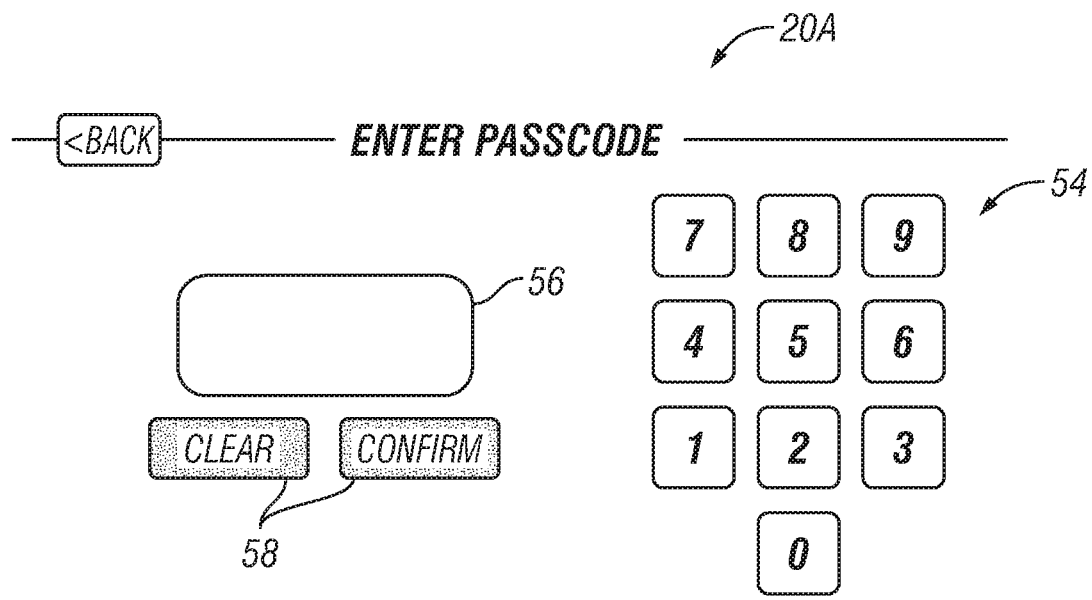
Figure 3B:
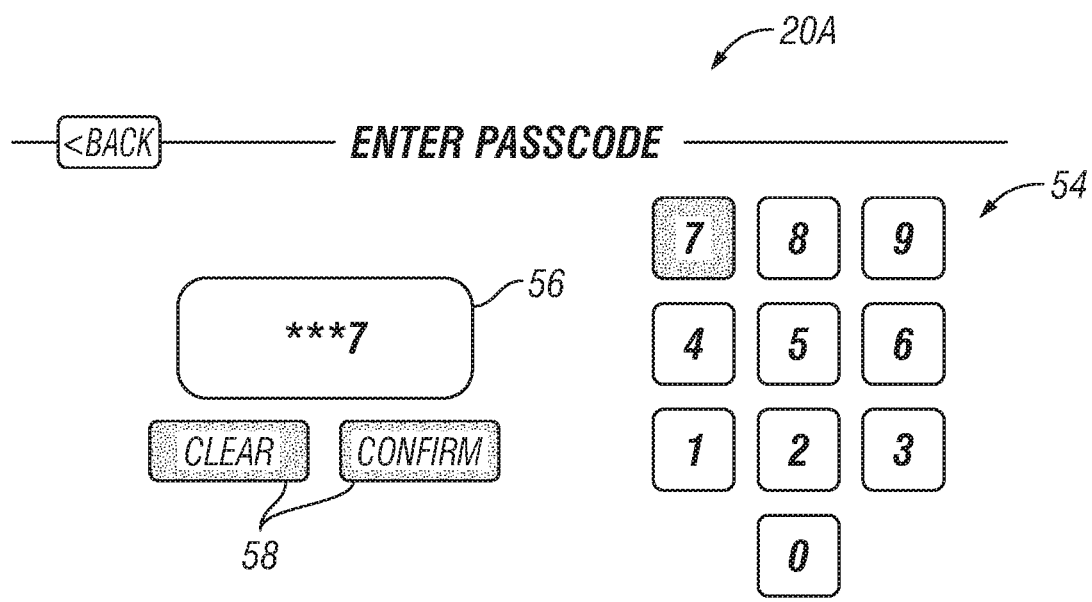
Figure 3C:
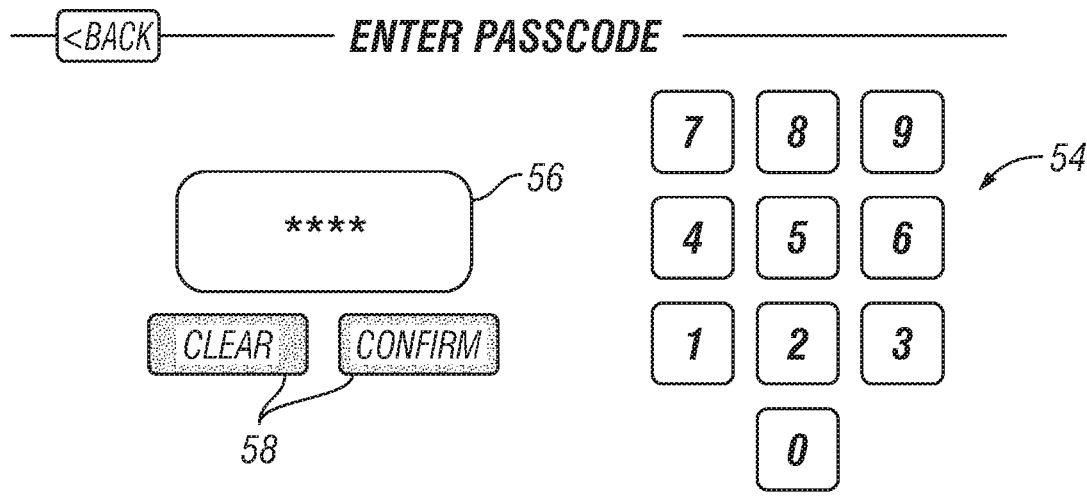
Figure 3D:
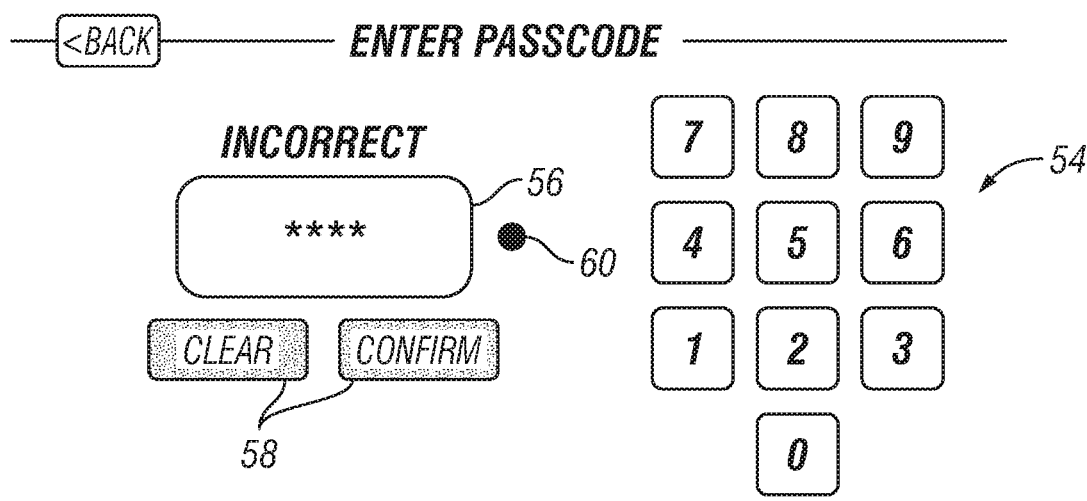
Figure 3E:
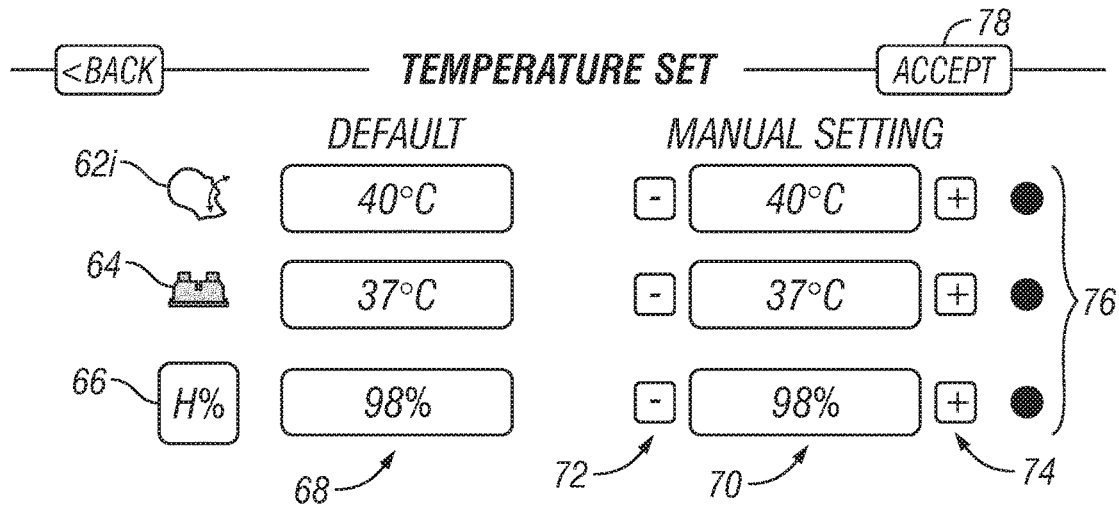
Figure 3F:
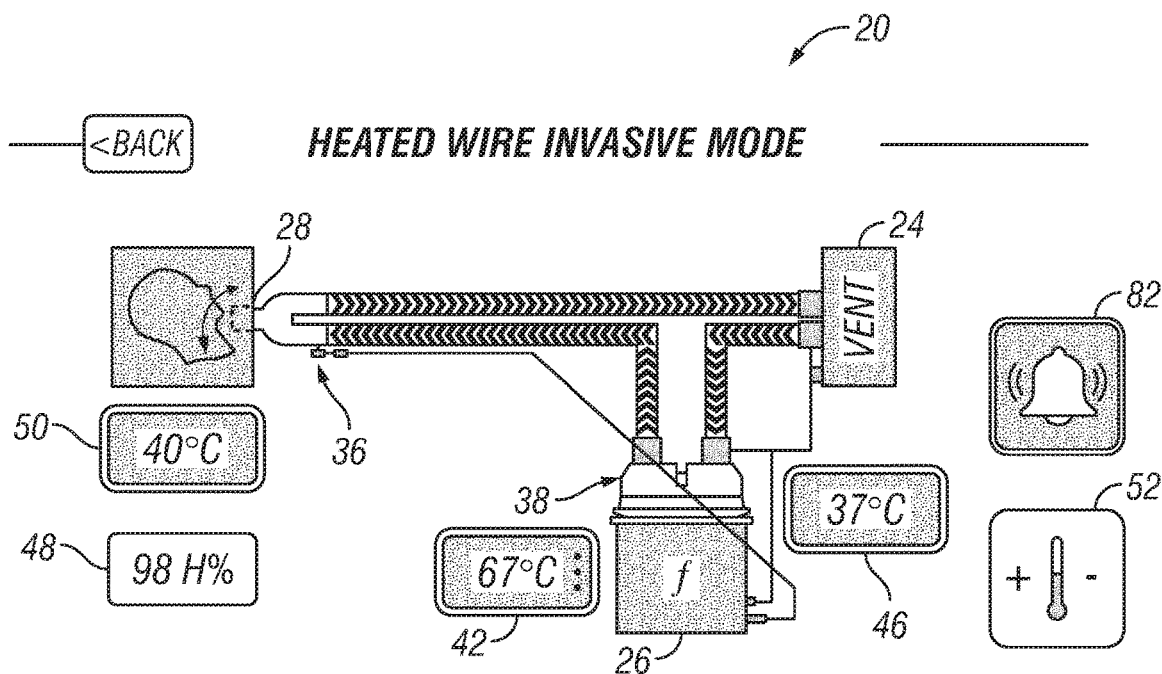

FIGS. 3 through 3F show examples of some of the operational screens that may appear on the touch screen after the user has selected the heated wire and invasive modes.

After those modes have been selected, a complete heated/invasive system diagram 20*i* will appear as seen in FIG. 3. This system diagram shows schematic images of: a ventilation device 24, humidifier 26, invasive patient airway device 28*i*, first inspiratory gas conduit 30 running from the ventilation device 24 to the inlet of the humidifier 26, second inspiratory gas conduit running from the humidifier outlet to the invasive patient airway device 28*i*, an exhalation conduit 34 running from the invasive patient airway device 28*i* to the ventilation device 24, a first temperature sensor icon 42 showing the sensed temperature of the humidifier heating element (e.g., heating plate), a second temperature sensor icon 46 showing the sensed temperature the humidified inspiratory gases at or near the location where the second inspiratory gas conduit 32 connects to the outlet of the humidifier 26, a third temperature sensor icon 50 showing the sensed temperature of humidified inspiratory gases at or near the location at which the second inspiratory gas conduit 32 connects to the invasive patient airway device 28*i*, a humidity sensor icon 48 showing the sensed humidity of humidified inspiratory gases at or near the location at which the second inspiratory gas conduit 32 connects to the invasive patient airway device 28*i* and a setting change icon 52 which may be touched by the user if it is desired to change any of the operational settings such as target temperature or humidity settings.

If the user touches the setting change icon 52, a passcode entry screen 20*a* will appear as shown in FIG. 3A. The user then uses keypad 54 to enter a passcode and the entered passcode appears in passcode screen 56, as illustrated in FIG. 3B. The user then touches either the clear or confirm icon 58 depending on whether the user believes the correct passcode to have been entered. If the entered passcode does not match an acceptable passcode that has been programmed to the controller, an incorrect passcode indicator 60 will appear as seen in FIG. 3C.

If the entered passcode does match an acceptable passcode that has been programmed to the controller, a secure setting modification screen will appear as seen in FIG. 3D. That secure setting modification screen shows a first column of default setting icons 68 which display the default settings for patient airway temperature 62*i* (i.e., the temperature of humidified inspired gases at or near the location at which the second inspiratory gas conduit 32 connects to the invasive patient airway device 28*i* as sensed by the third temperature sensor), humidifier temperature 64 (i.e., the temperature of humidified inspired gases at or near the location at which the second inspiratory gas conduit 32 connects to the outlet of the humidifier as sensed by the second temperature sensor) and patient airway humidity 66 (i.e., the relative humidity of humidified inspired gases at or near the location at which the second inspiratory gas conduit 32 connects to the invasive patient airway device 28*i* as sensed by the humidity sensor). Adjacent to each of these default setting icons 68 is a column of corresponding manual setting icons 70. Each of the manual setting icons 70 has an associated raise setting icon 74, an associated lower setting icon 74 and a manual setting override indicator 76. Initially, the default temperature and humidity settings will appear in both the default setting icons 68 and manual setting icons 70 and the manual setting override icons will not be illuminated. If the user wishes to manually override any of the default settings, the user will selectively touch either the raise icon 72 or lower icon 74 to cause the desired manual override setting to appear in each manual setting icon 70 for which manual override of the default setting is desired with illumination of the associated manual override indicator icon 76, within the clinically acceptable range. In at least some embodiments of the invention, the manual override indicator 76 may emit different signal modalities (e.g., different colors of light) to indicate different states or conditions. For example, the manual override indicator 76 may emit green light when the user has selected a manual override setting that is within an acceptable range for that variable. However, if the user selects a manual override value that is outside of the acceptable range, the manual override indicator 76 may emit red light and/or the processor may cause the input manual override value to stop at or adjust to the closest value that is within the acceptable range (i.e., the subject manual setting icon 74 will stop at or automatically adjust to the lowest value in the acceptable range when the user attempts to enter a setting that is below the acceptable range and will stop at or automatically adjust to the highest value in the acceptable range when the user attempts to enter a setting that is above the acceptable range.

After manual override settings within the acceptable range have been entered, the user touches the accept icon 78 and the controller will then reset to the manual override settings and the touch screen display will once again show the schematic diagram of the system as indicated in FIG. 3E. The user may then observe the sensed temperatures and humidity displayed by icons 42, 46, 48 and 50 as described above. If any of the sensed temperatures or humidity deviate more than a pre-determined amount from the settings that have been entered to the controller, the controller will cause an alarm icon 82 to illuminate and (optionally) a corresponding audible or other alarm signal may be emitted. This may occur as an alarm if any sensed temperature or humidity changes by a pre-programmed significant amount for an unexpected reason and not if the user is trying to manually select a temperature or humidity outside of the limited range that is provided as a choice.

The controller may be programmed to cause the alarm icon 82 to illuminate and/or emit an audible or other suitable signal if any sensor reading is different than what is selected/default setting. Also, the controller may cause the area of concern (i.e., whichever sensed value that has triggered the alarm) to flash or be otherwise highlighted or indicated on the touch screen display. Also, in at least some embodiments of the invention where the alarm emits an audible signal, the user may cause the audible signal to be muted for a period of time (e.g., one minute) by taking some volitional muting action such as by touching the alarm icon 82. When so muted, the audible alarm signal may re-commence after the timed muting period has expired if the problem that triggered the alarm has not been rectified.

Figure 4:
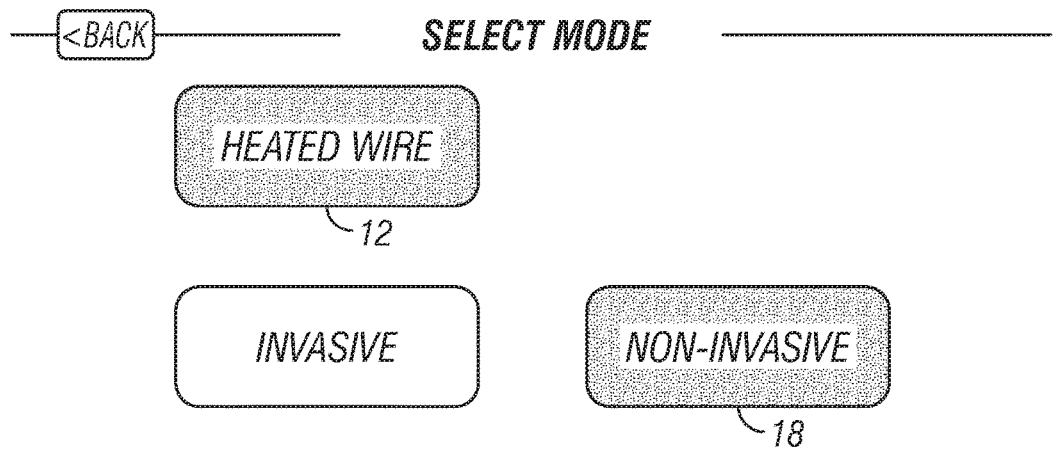
FIGS. 4 through 4B are examples of some of the operational screens that may appear on a touch screen user interface of a system of the present invention after a user has selected to operate the system in HEATED/NON-INVASIVE mode.
Figure 4A:
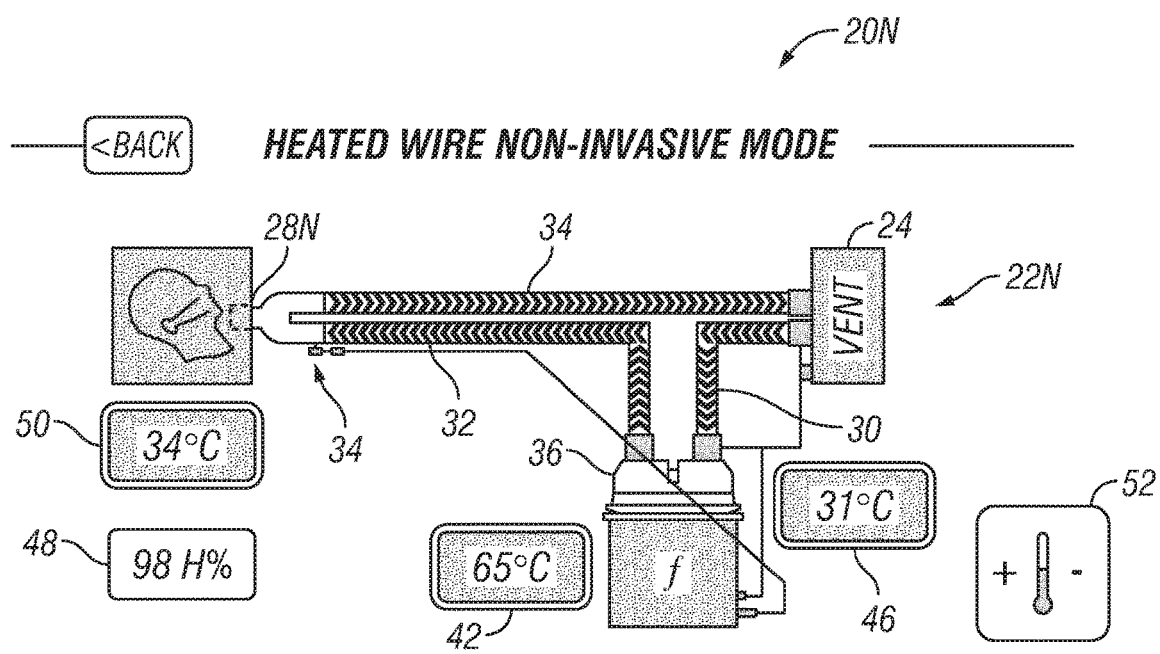
Figure 4B:
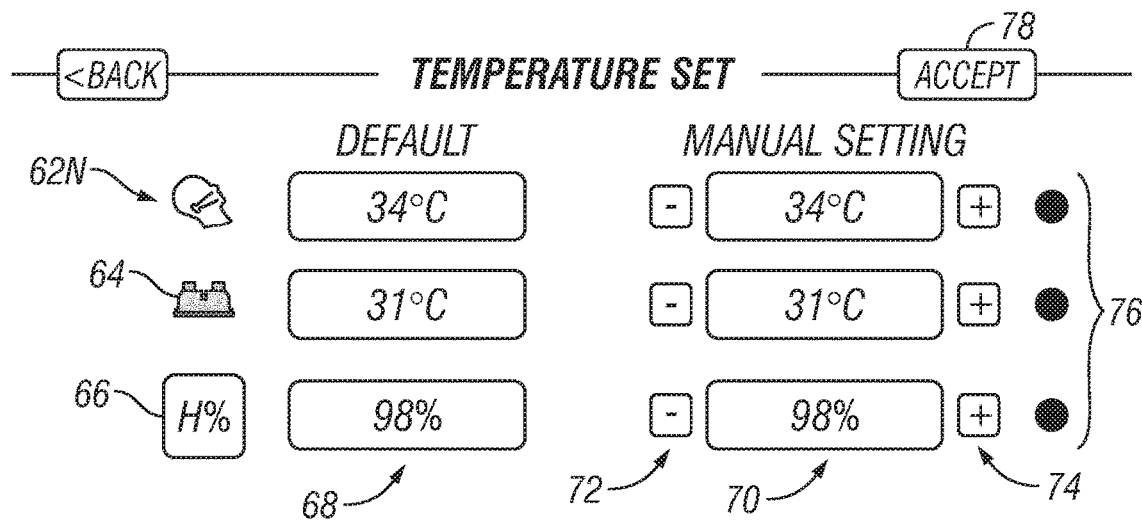

FIGS. 4 through 4B show the manner in which certain touch screen displays may vary from that described above if user initially selects to operate in heated wire/non-invasive mode. As shown on FIG. 4, the heated wire icon 12 and non-invasive icon 18 will illuminate when touched and, thereafter, a schematic system diagram 20*n* will appear as seen in FIG. 4A. This schematic system diagram screen 20*n* differs from that described above in relation to FIG. 3 only in that a non-invasive patient airway icon 28N appears instead of an invasive patient airway icon 28*i* as seen in FIG. 3. Also, if the user wishes to change a setting and enters a valid passcode which is accepted by the controller, a secure setting modification screen as shown in FIG. 4B will appear. This secure setting modification screen seen in FIG. 4B differs from that described above in relation to FIG. 3D only in that a non-invasive patient airway icon 62*n* appears in place of the invasive patient airway icon 62*i* seen in FIG.

3D. All other functions are the same as described above with respect to the heated wire/invasive mode of operation.

Figure 5:
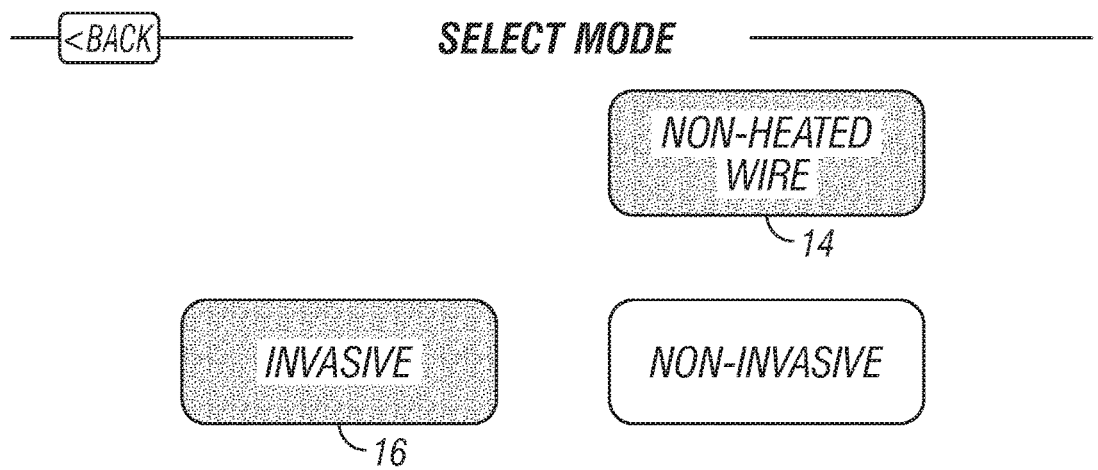
FIGS. 5 through 5B are examples of some of the operational screens that may appear on a touch screen user interface of a system of the present invention after a user has selected to operate the system in NON-HEATED/INVASIVE mode.
Figure 5A:
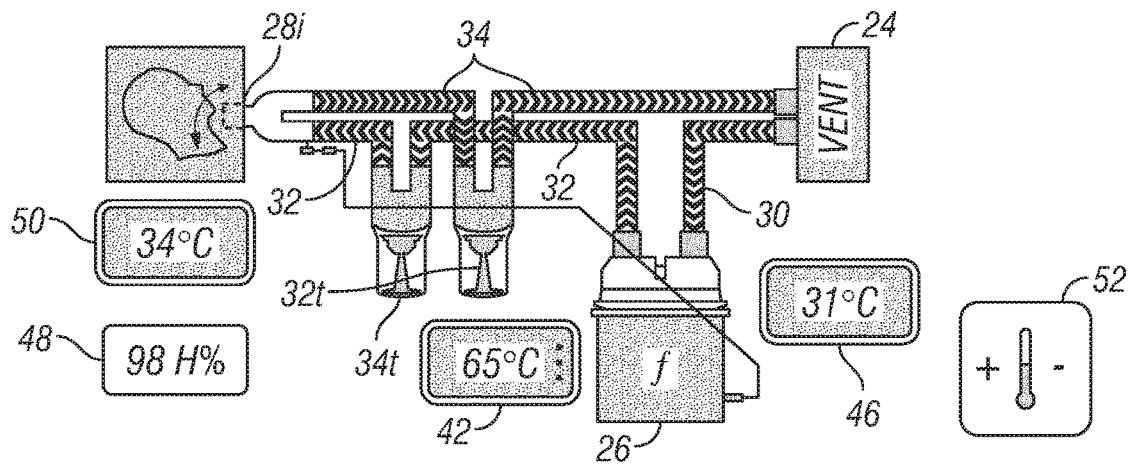
Figure 5B:
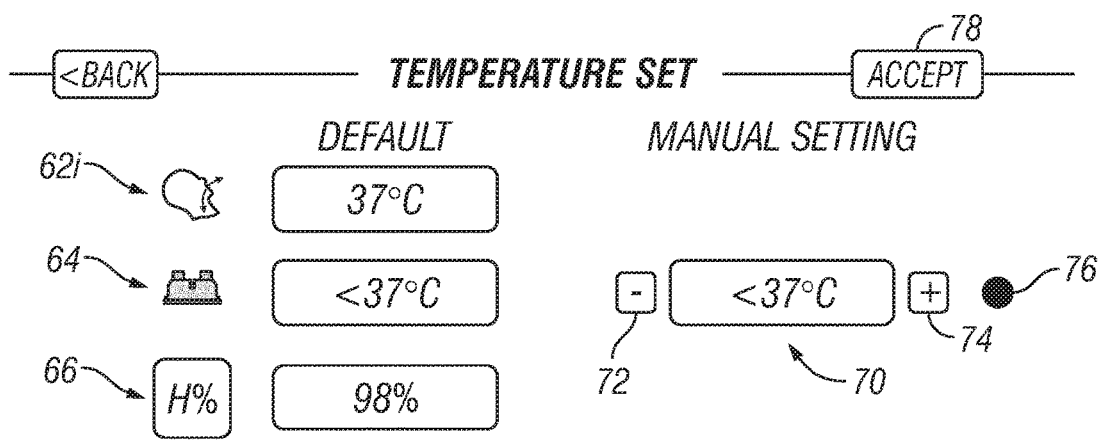

FIGS. 5 through 5B show the manner in which certain touch screen displays may vary from that described above if user initially selects to operate in non-heated wire/invasive mode. As shown in FIG. 5, the non-heated wire icon 14 and invasive icon 16 will illuminate when touched and, thereafter, a schematic system diagram 20i/n will appear as seen in FIG. 5A. This schematic system diagram screen 20i/n differs from that described above in relation to FIG. 3 only in that condensation traps 34T are shown in the second inspiratory gas conduit 32. Also, if the user wishes to change a setting and enters a valid passcode which is accepted by the controller, the secure setting modification screen as shown in FIG. 5B will appear. This secure setting modification screen of FIG. 5B differs from that described above in relation to FIG. 3D in that the only possible manual override is for the humidifier temperature 64. Since the inspired gas heating element is not operational in this mode, the default settings for patient airway temperature 62i and patient airway humidity 66 cannot be manually overridden. However, the controller may be programmed to automatically adjust the default settings displayed for the patient airway temperature 62i and patient airway humidity 66 so that they correspond to the manual setting entered by the user for humidifier temperature 64. All other functions are the same as described above with respect to the heated wire/invasive mode of operation.

Figure 6:
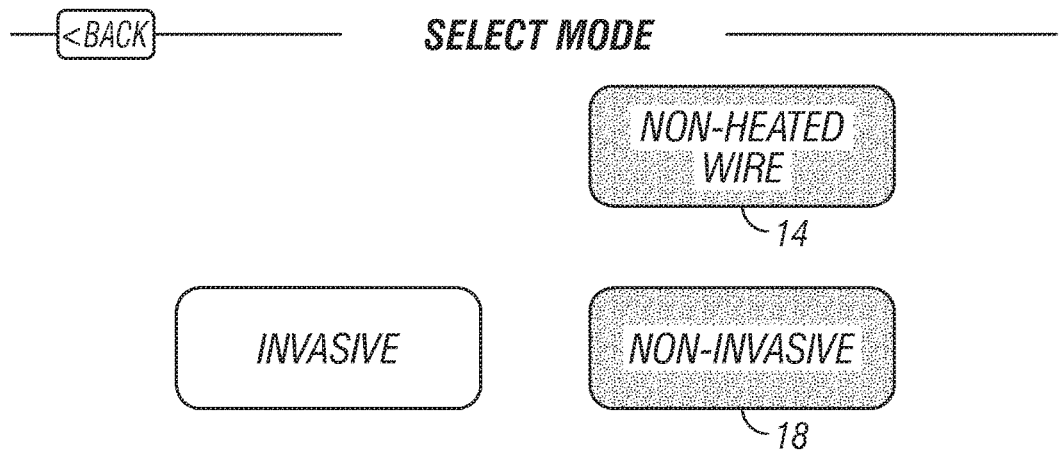
FIGS. 6 through 6B are examples of some of the operational screens that may appear on a touch screen user interface of a system of the present invention after a user has selected to operate the system in NON-HEATED/NON-INVASIVE mode.
Figure 6A:
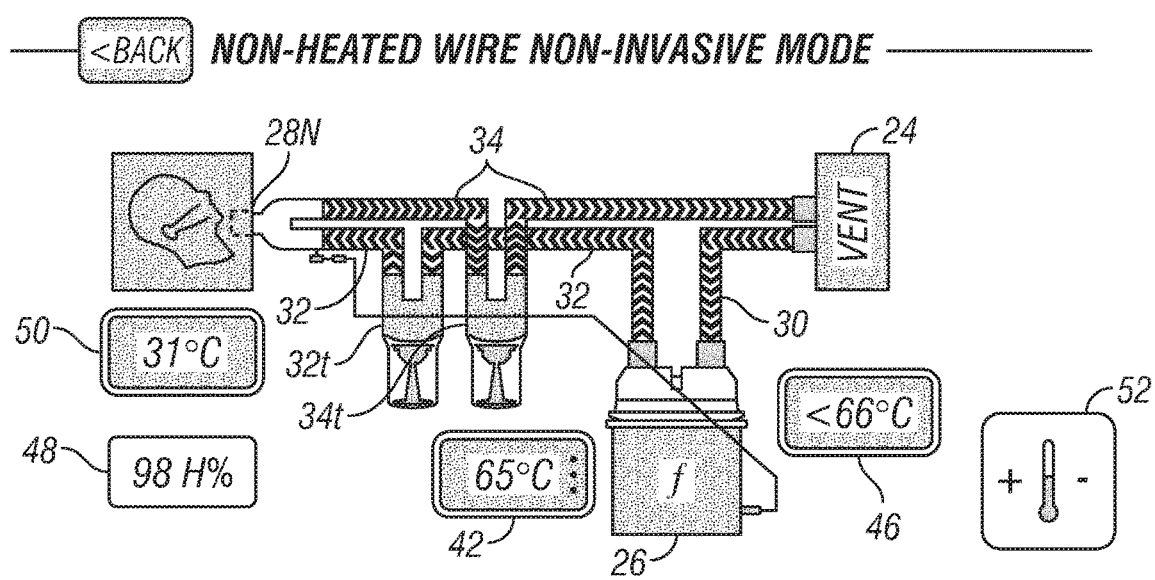
Figure 6B:
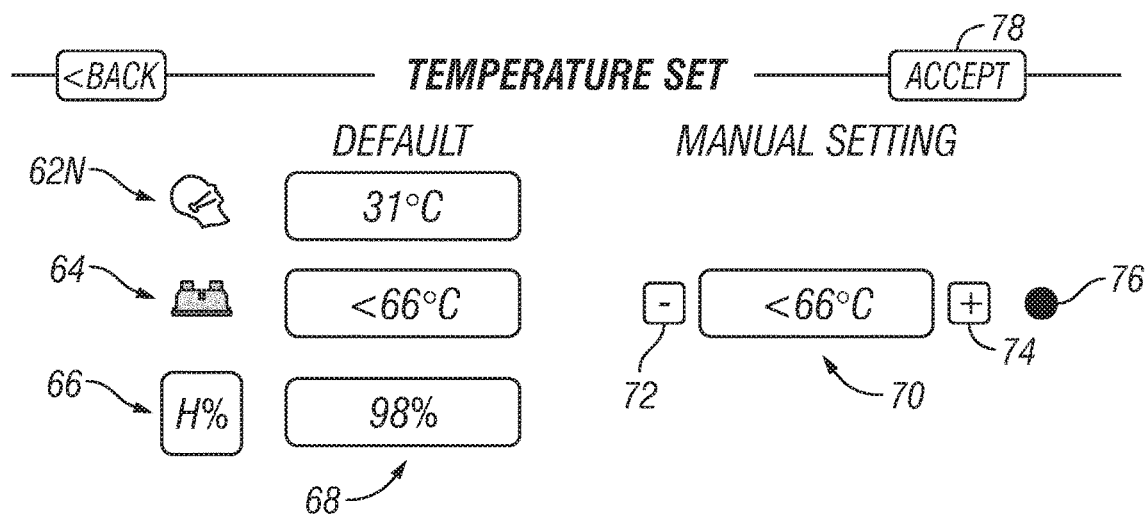
Figure 7:
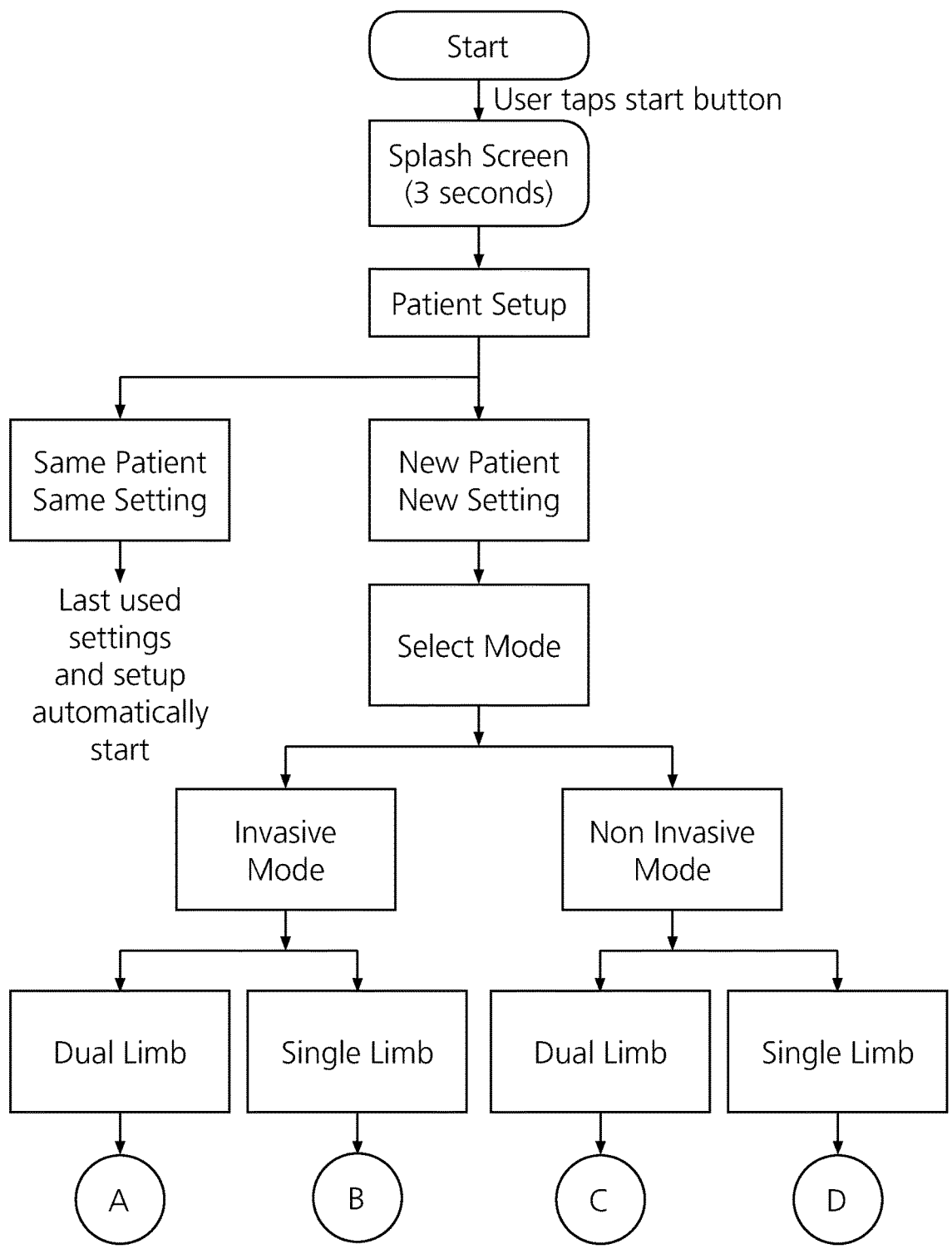
FIG. 7 is a flow diagram showing the initiation of the interface providing information on the use of the present invention and the sequence of the operational screens for the user to configure and confirm the settings. Based on the selection made, further relevant configuration options will be shown, as illustrated in FIGS. 8 to 11.
Figure 8:
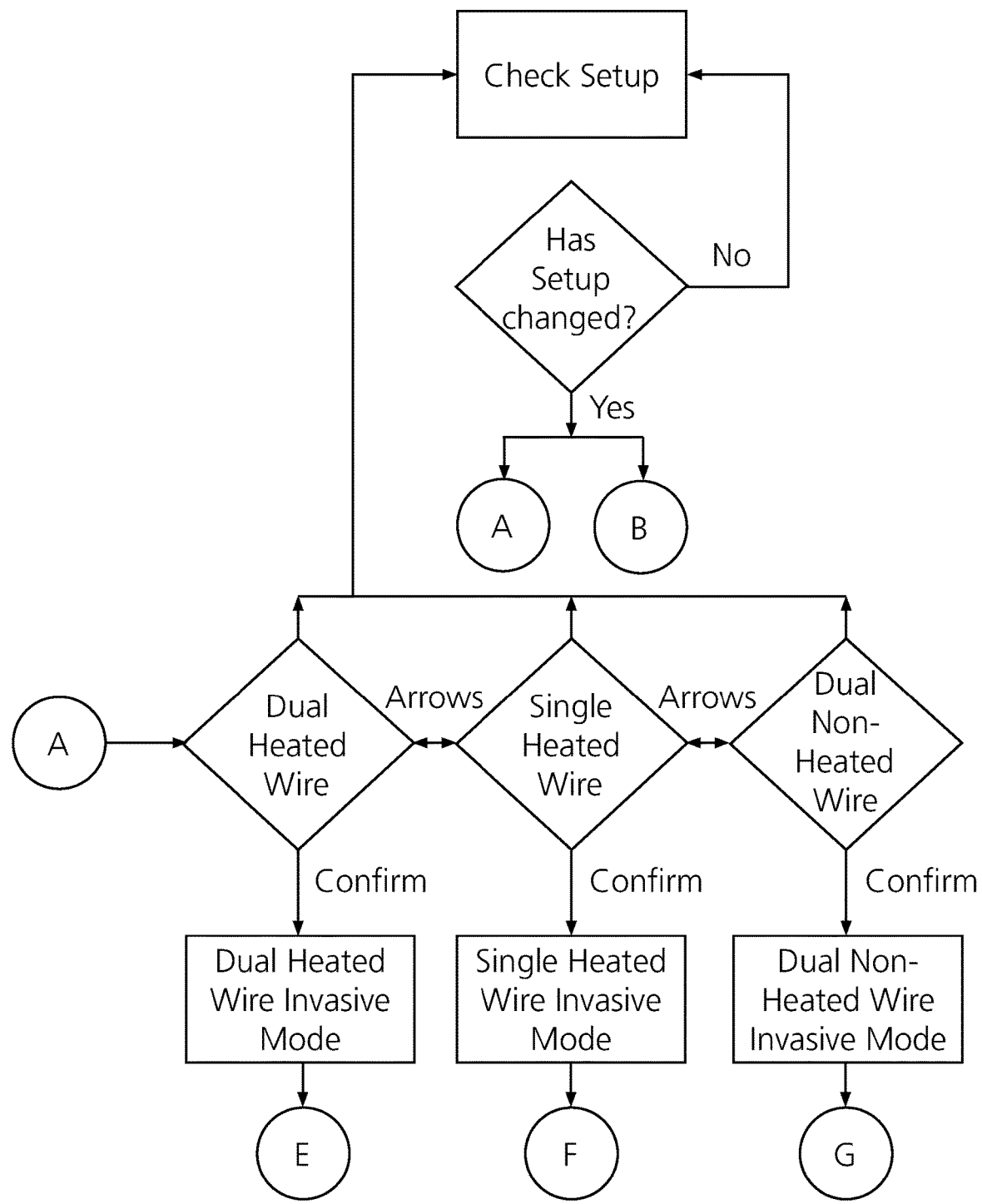
FIG. 8 is a flow diagram showing the operational screens for the user to further configure the settings to match the intended device to be used. The operational screens allow the user to cycle through setting options, confirm selection or return to a previously viewed screen.
Figure 9:
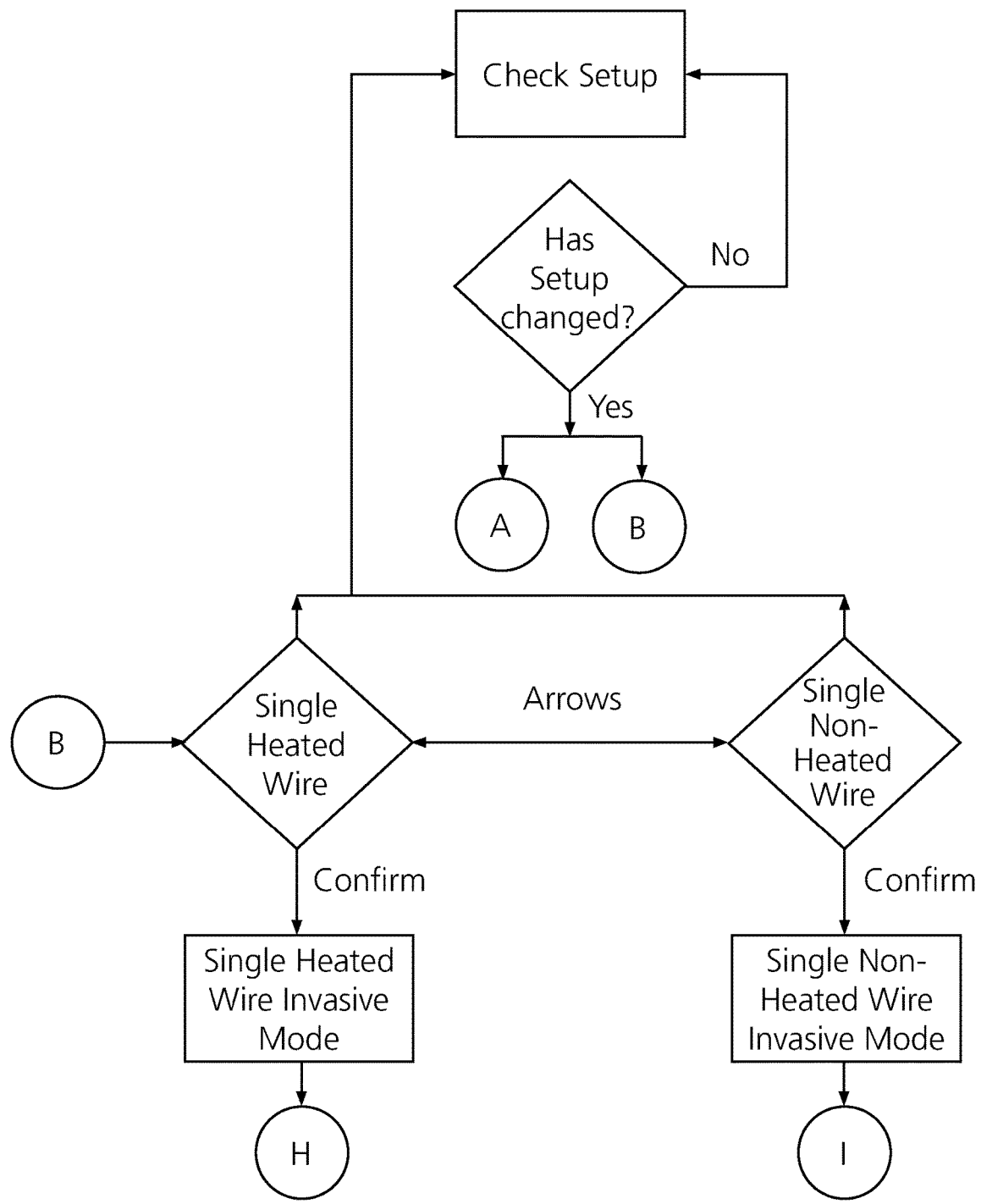
FIG. 9 is a flow diagram showing the operational screens for the user to further configure the settings to match the intended device to be used. The operational screens allow the user to cycle through setting options, confirm selection or return to a previously viewed screen.
Figure 10:
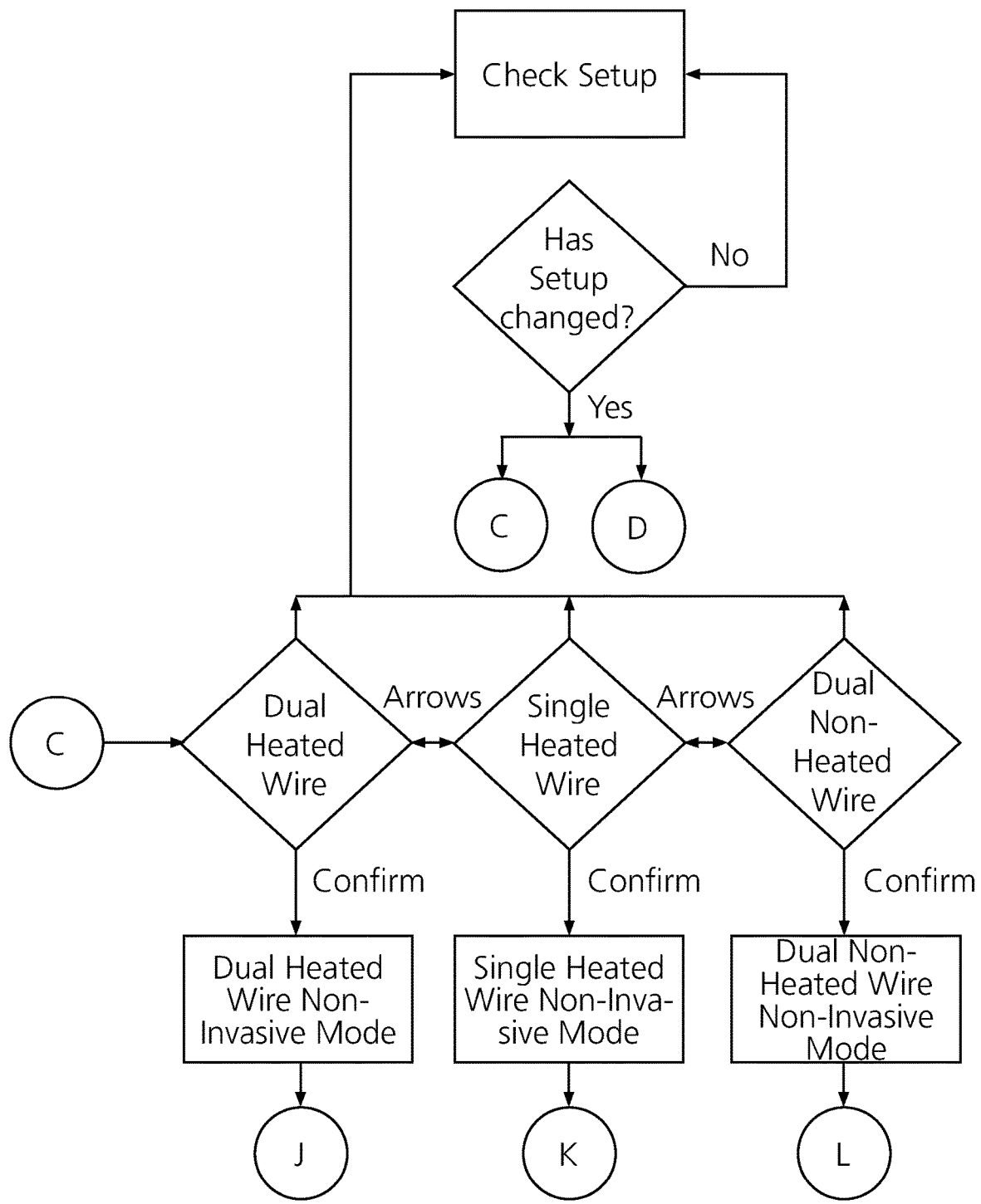
FIG. 10 is a flow diagram showing the operational screens for the user to further configure the settings to match the intended device to be used. The operational screens allow the user to cycle through setting options, confirm selection or return to a previously viewed screen.
Figure 11:
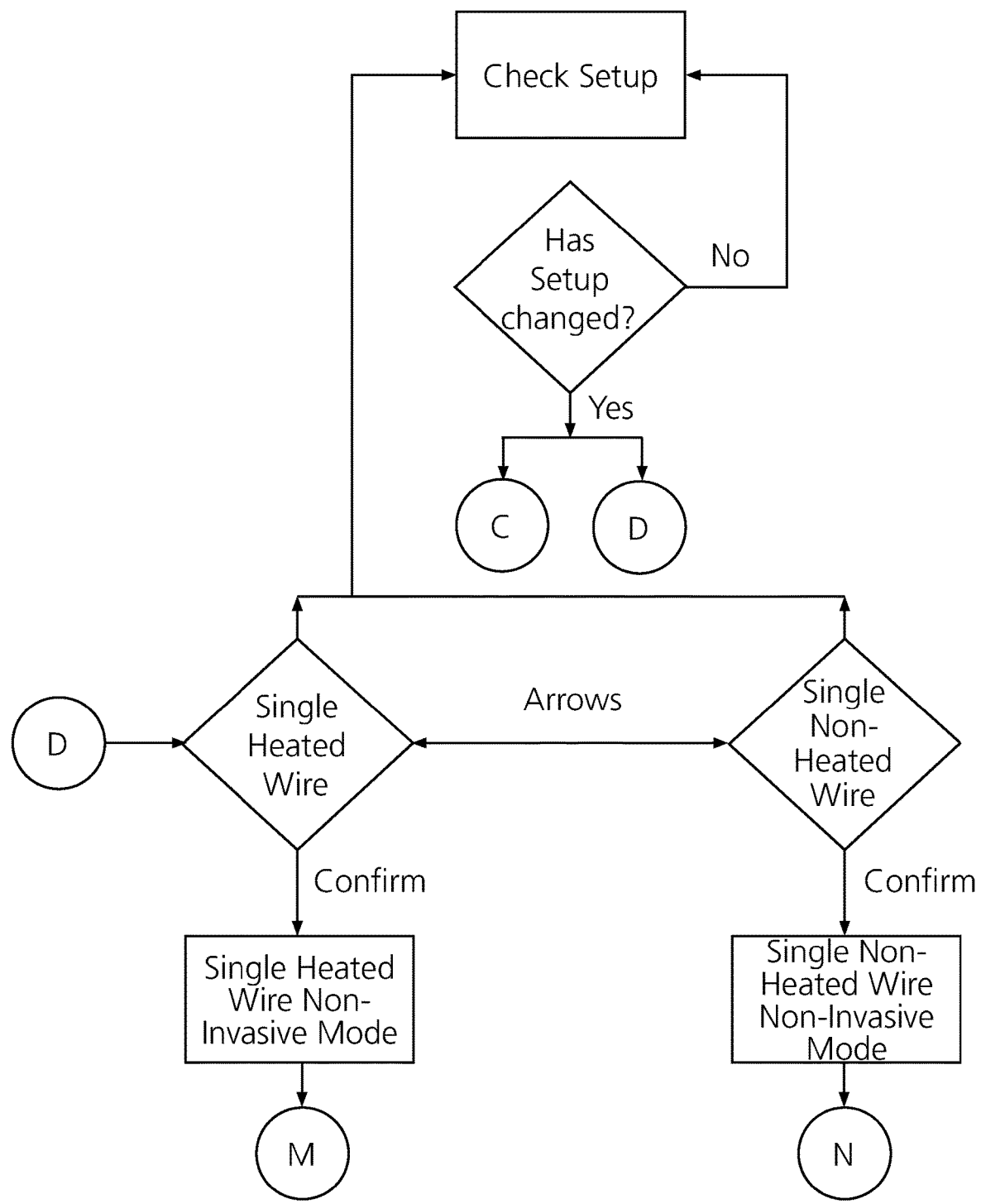
FIG. 11 is a flow diagram showing the operational screens for the user to further configure the settings to match the intended device to be used. The operational screens allow the user to cycle through setting options, confirm selection or return to a previously viewed screen.
Figure 12:
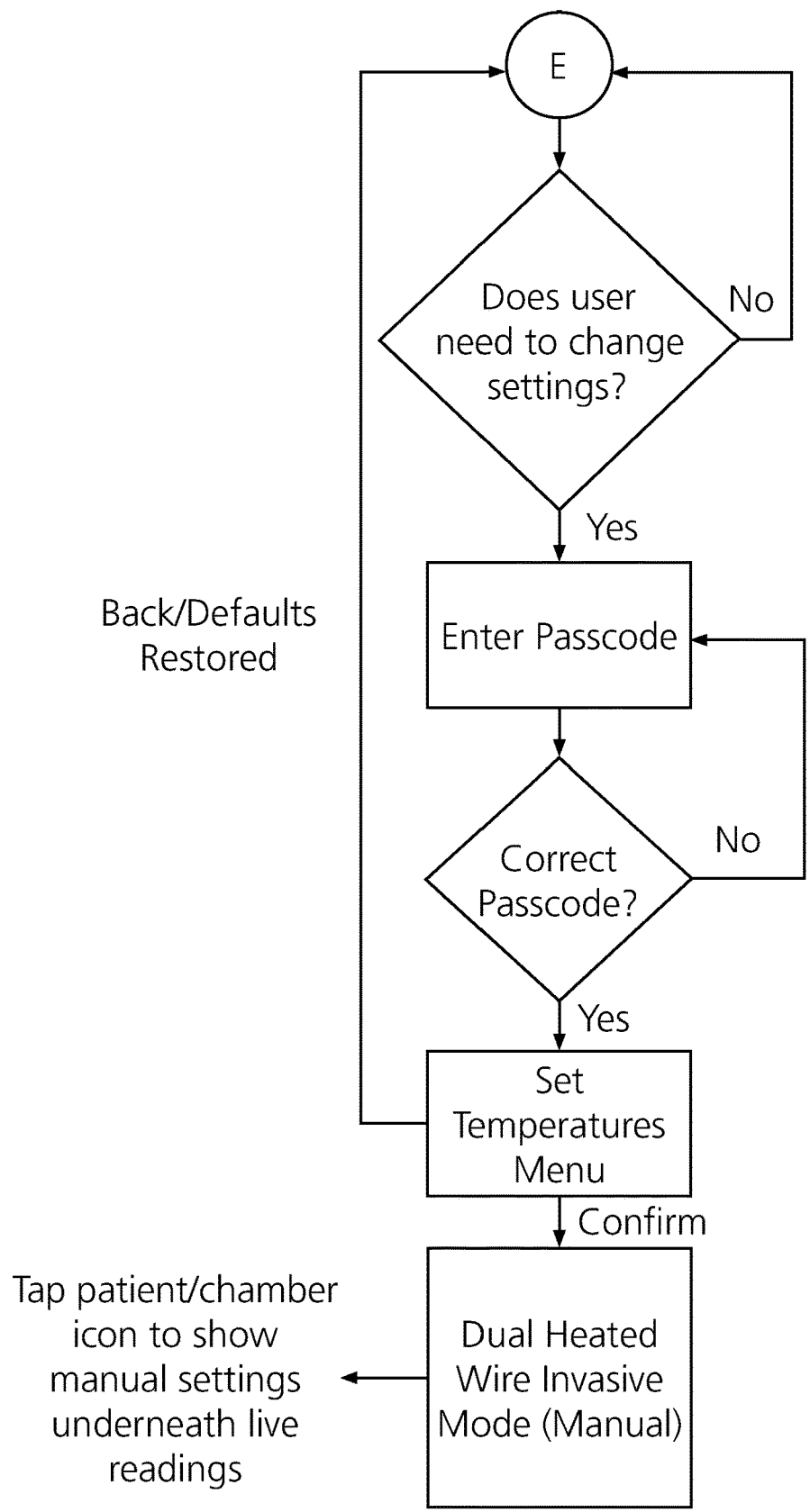
FIG. 12 is a flow diagram showing the operational screens for the user to amend the default settings for the mode selected in FIG. 8. Both the real-time measurements and settings can be simultaneously displayed.
Figure 13:
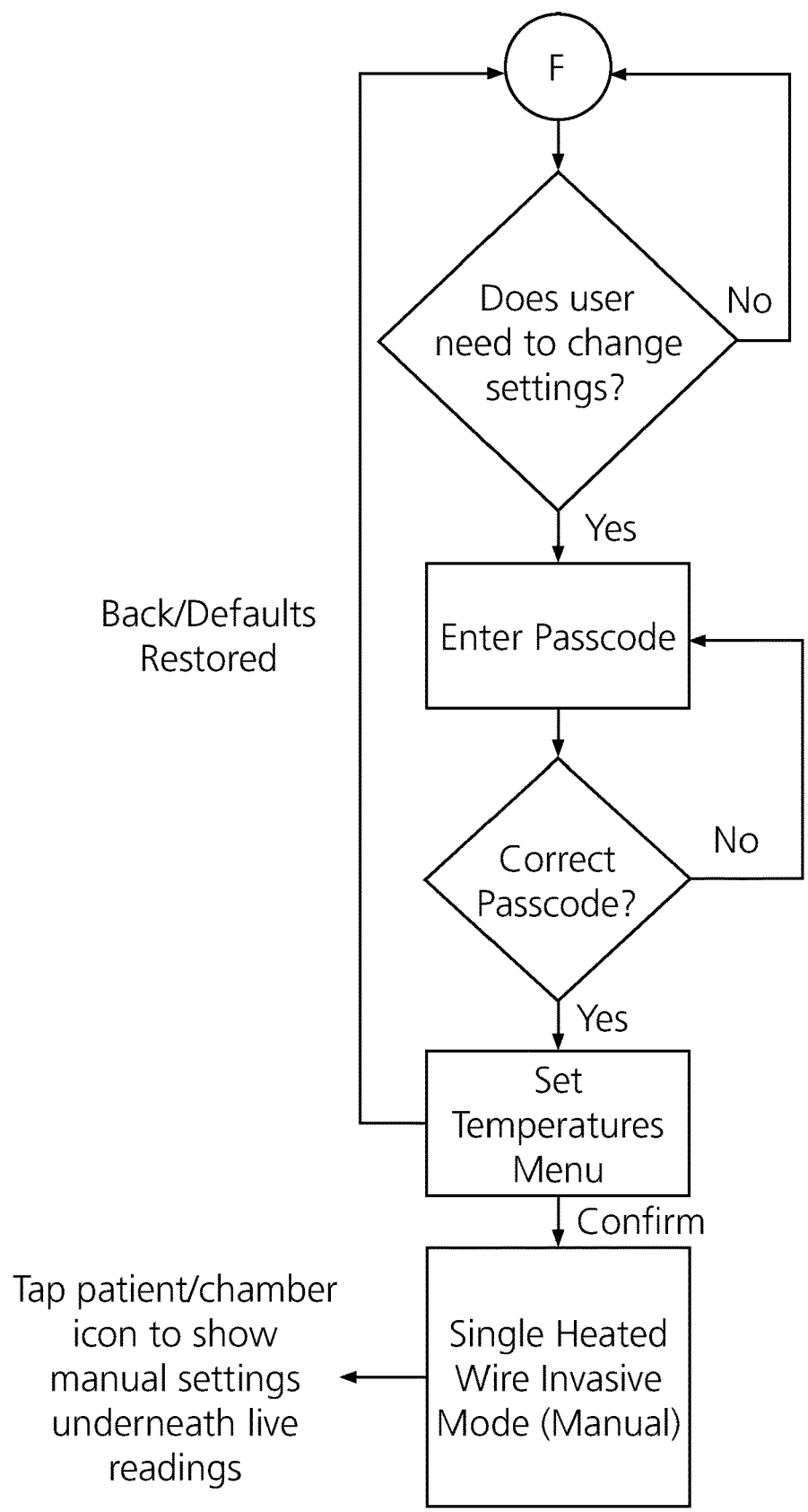
FIG. 13 is a flow diagram showing the operational screens for the user to amend the default settings for the mode selected in FIG. 8. Both the real-time measurements and settings can be simultaneously displayed.
Figure 14:
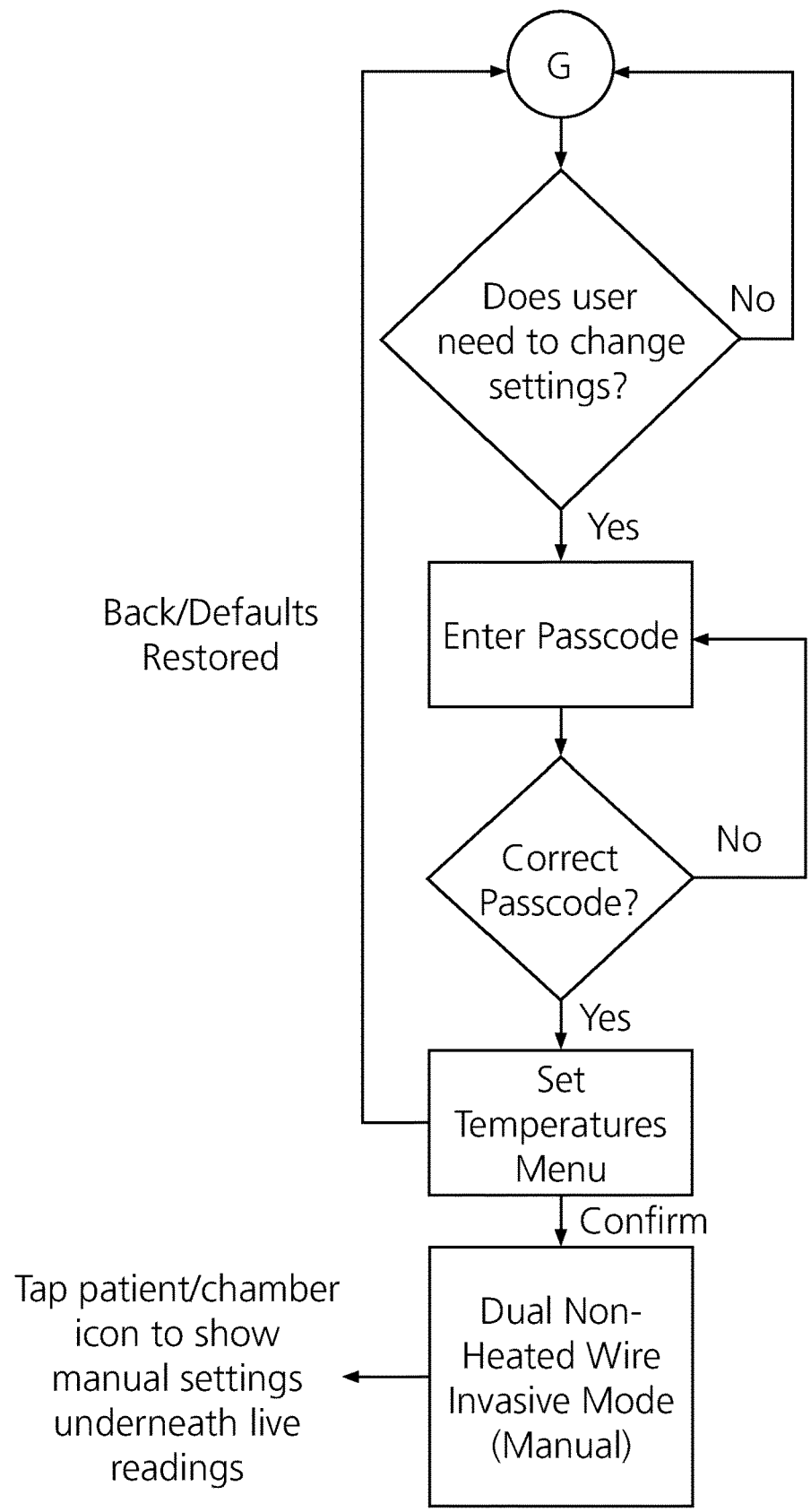
FIG. 14 is a flow diagram showing the operational screens for the user to amend the default settings for the mode selected in FIG. 8. Both the real-time measurements and settings can be simultaneously displayed.
Figure 15:
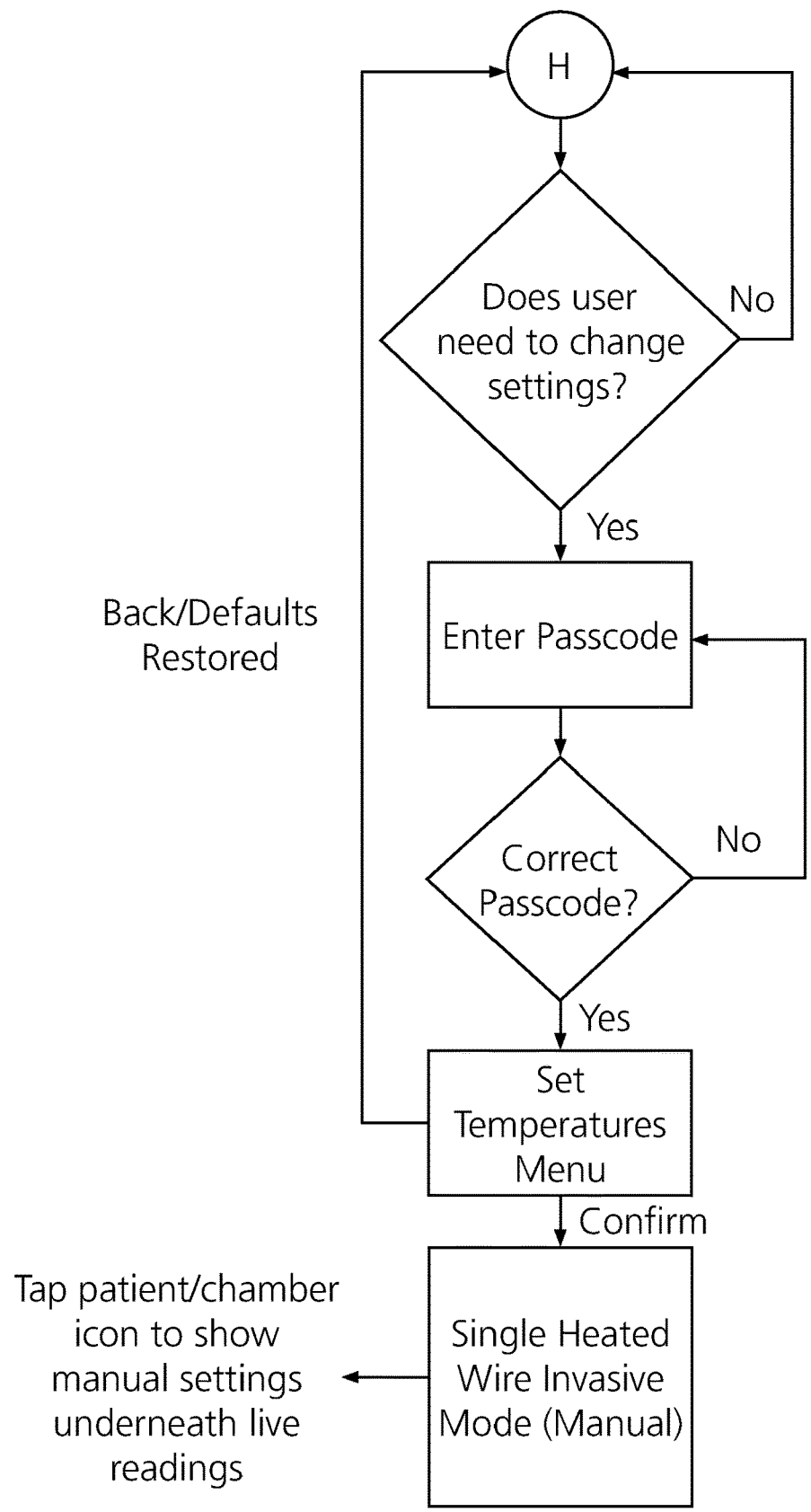
FIG. 15 is a flow diagram showing the operational screens for the user to amend the default settings for the mode selected in FIG. 9. Both the real-time measurements and settings can be simultaneously displayed.
Figure 16:
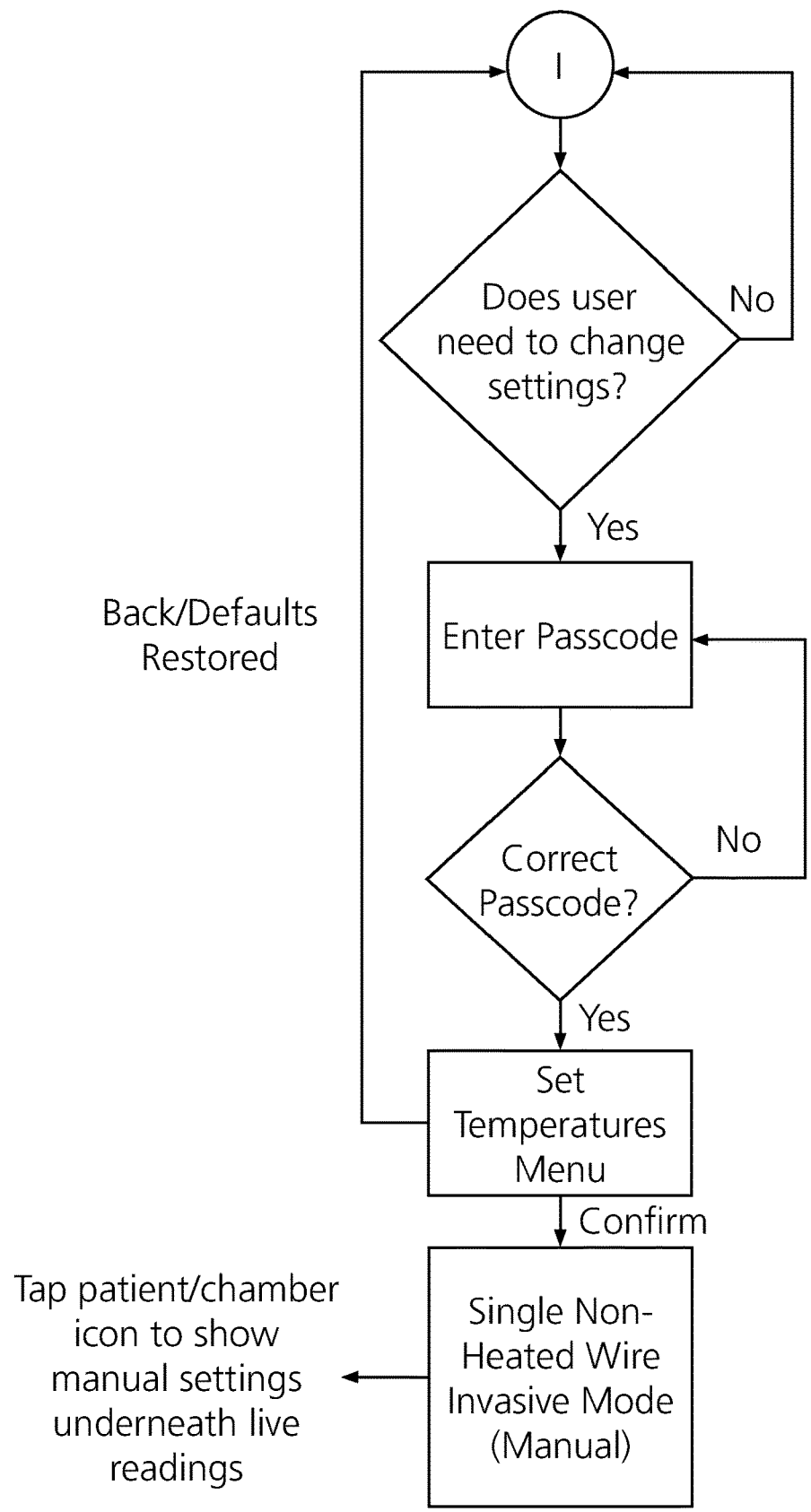
FIG. 16 is a flow diagram showing the operational screens for the user to amend the default settings for the mode selected in FIG. 9. Both the real-time measurements and settings can be simultaneously displayed.
Figure 17:
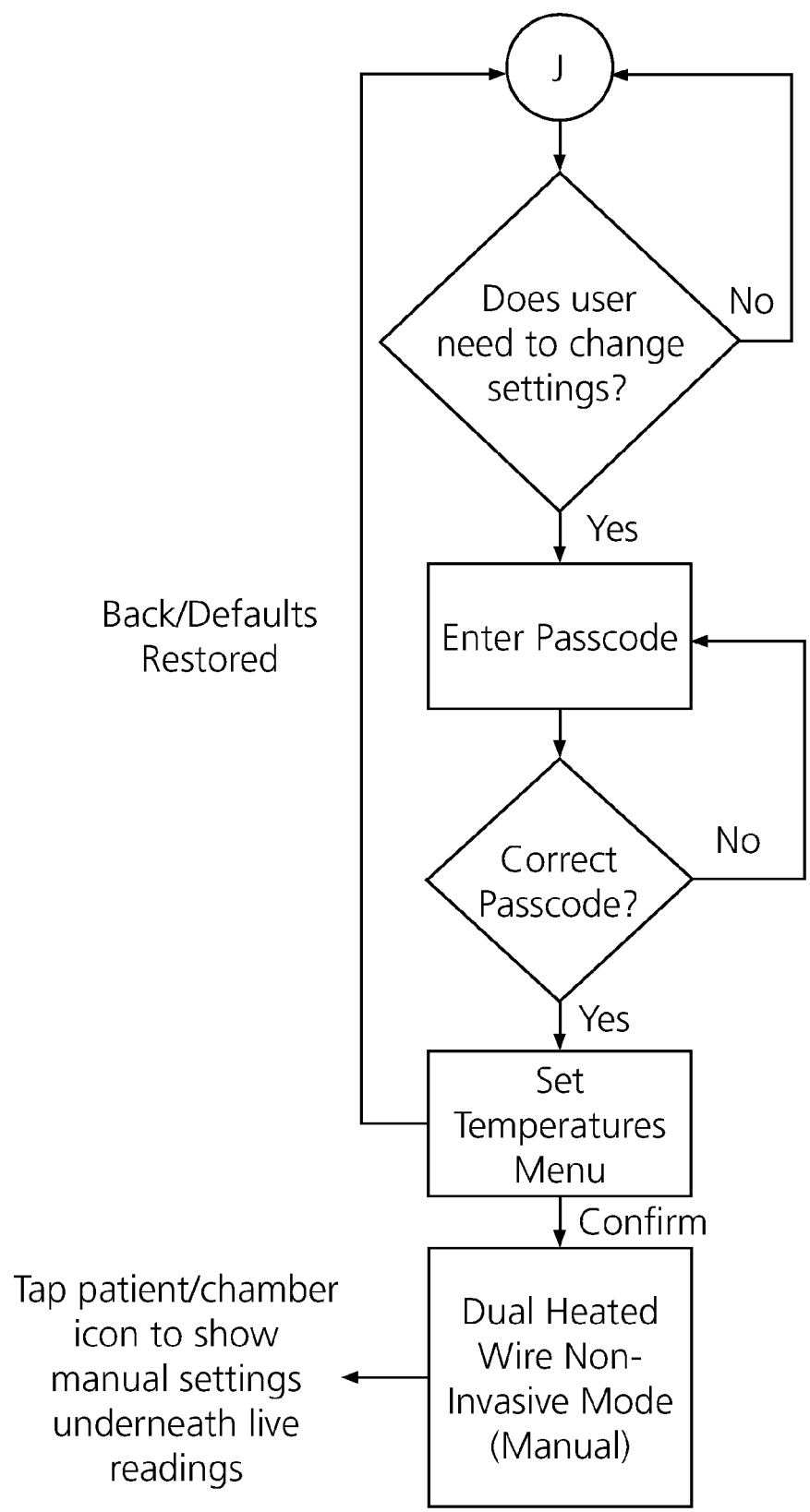
FIG. 17 is a flow diagram showing the operational screens for the user to amend the default settings for the mode selected in FIG. 10. Both the real-time measurements and settings can be simultaneously displayed.
Figure 18:
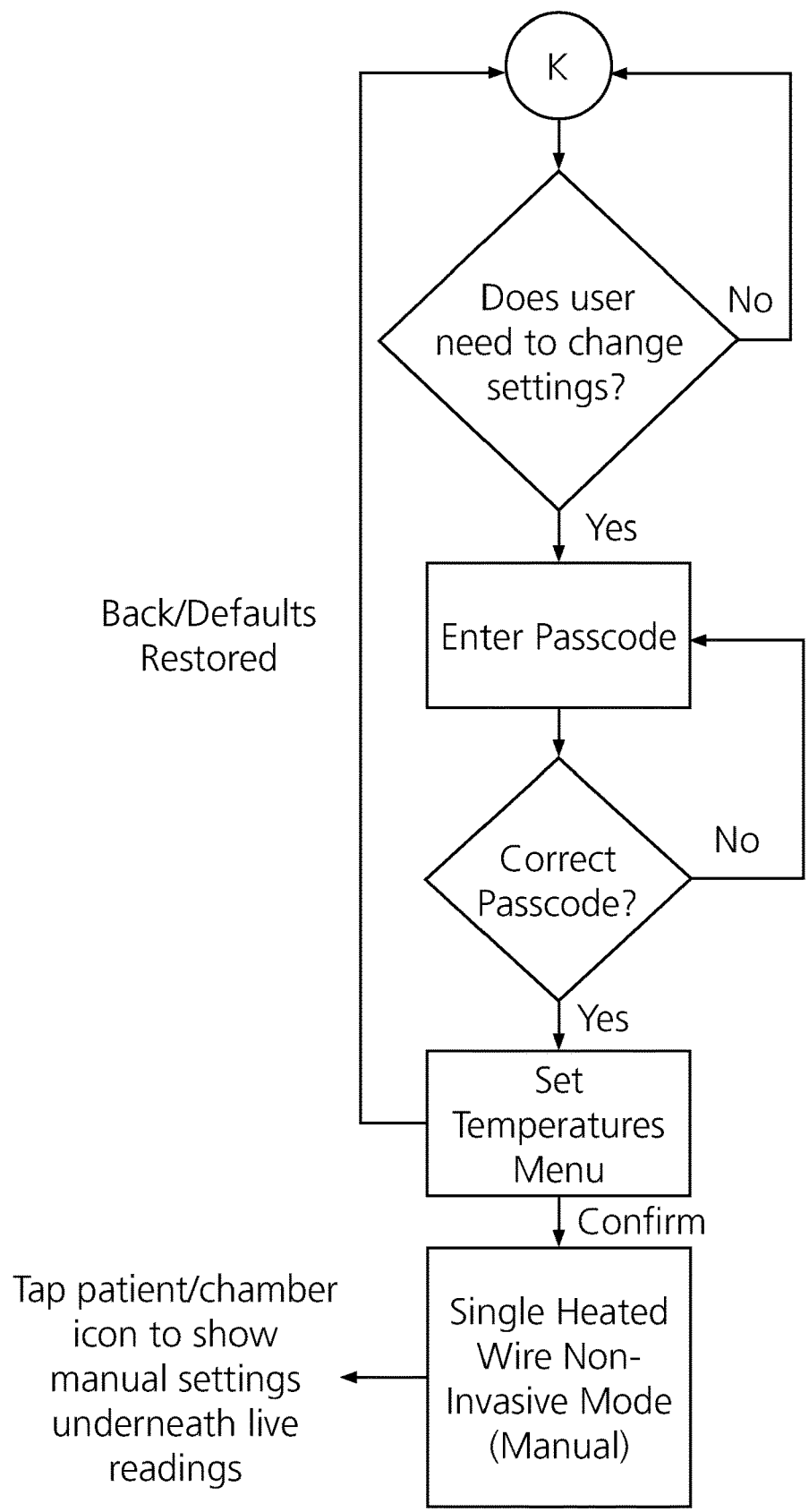
FIG. 18 is a flow diagram showing the operational screens for the user to amend the default settings for the mode selected in FIG. 10. Both the real-time measurements and settings can be simultaneously displayed.
Figure 19:
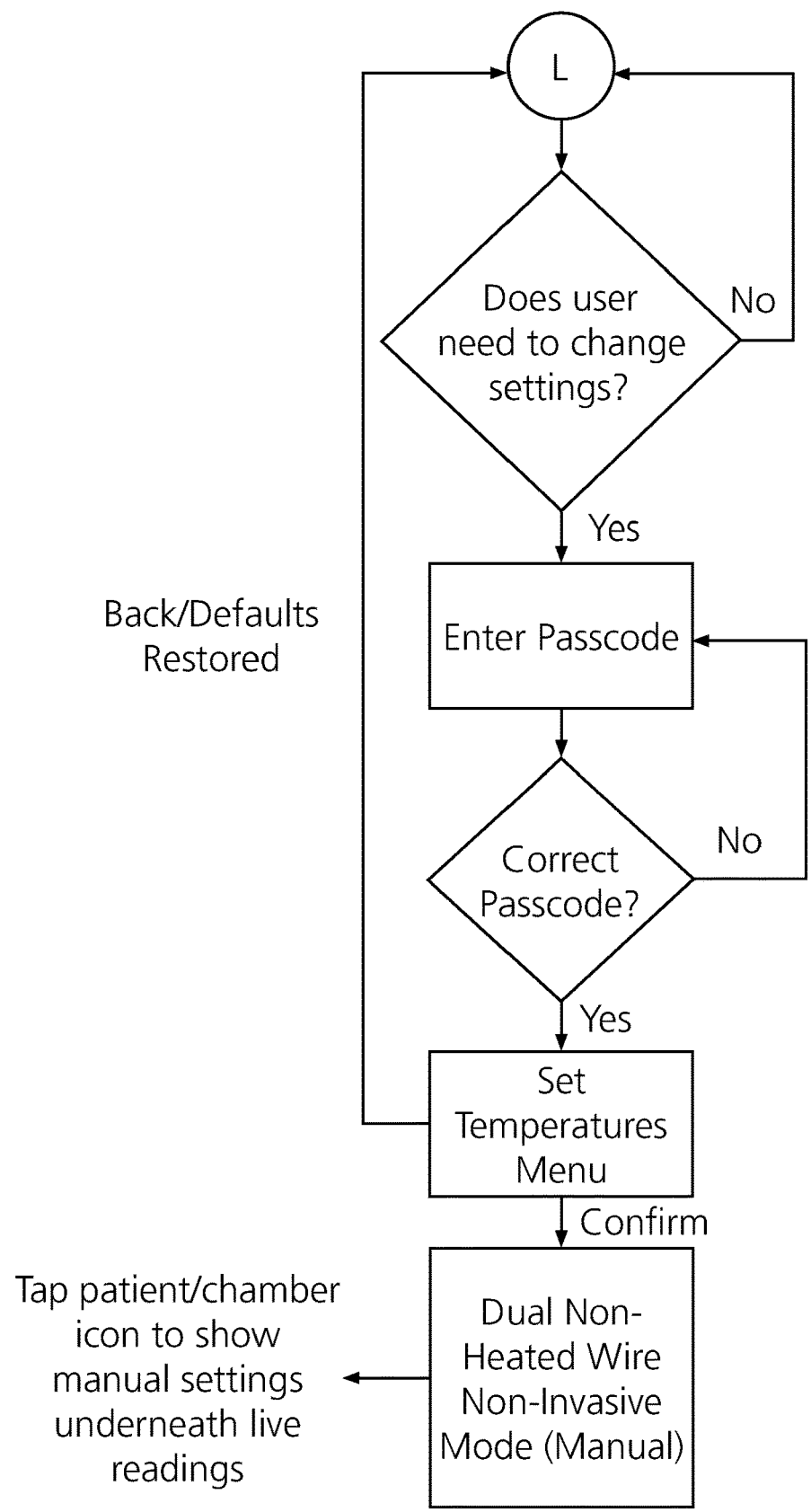
FIG. 19 is a flow diagram showing the operational screens for the user to amend the default settings for the mode selected in FIG. 10. Both the real-time measurements and settings can be simultaneously displayed.
Figure 20:
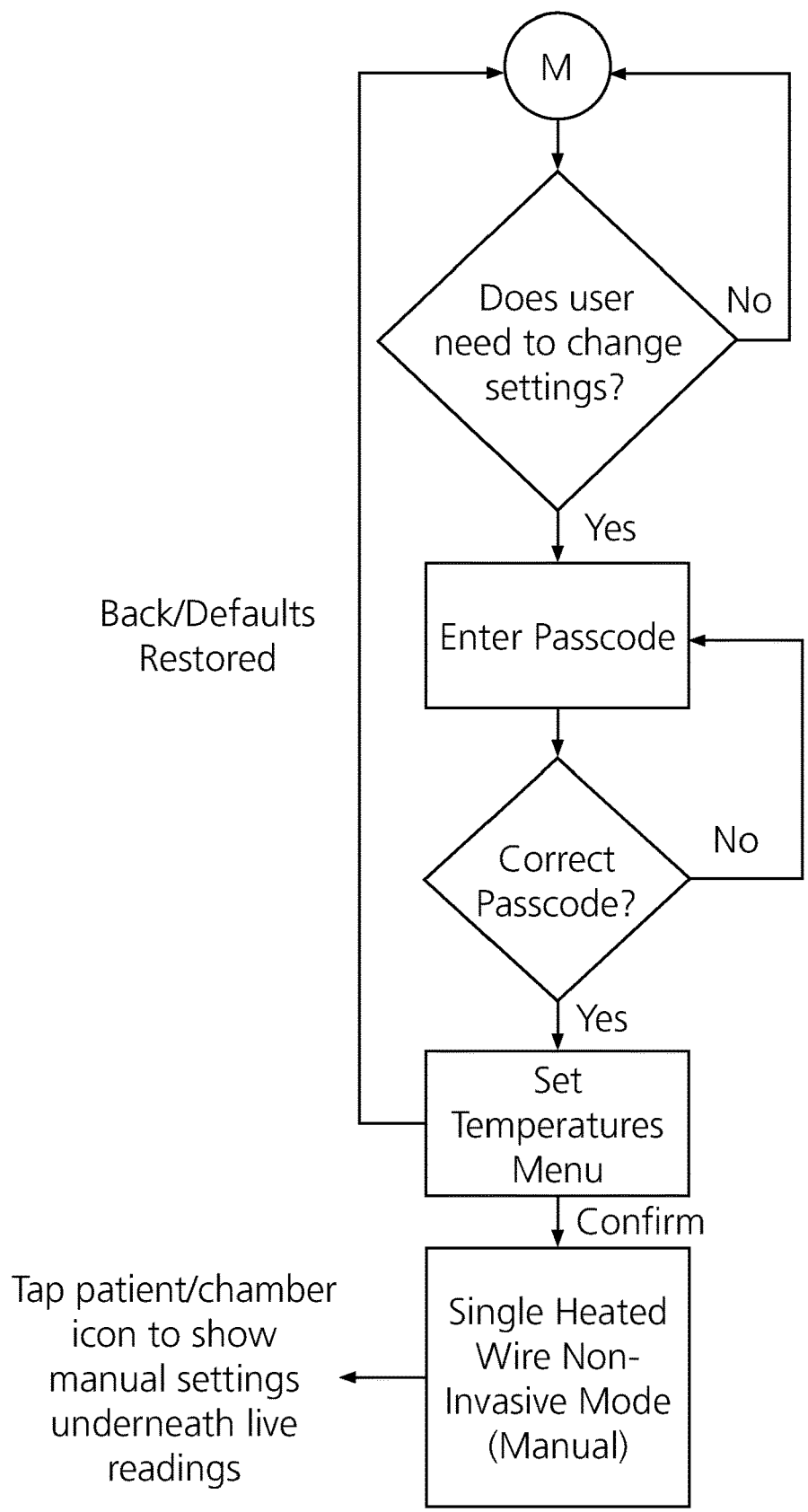
FIG. 20 is a flow diagram showing the operational screens for the user to amend the default settings for the mode selected in FIG. 11. Both the real-time measurements and settings can be simultaneously displayed.
Figure 21:
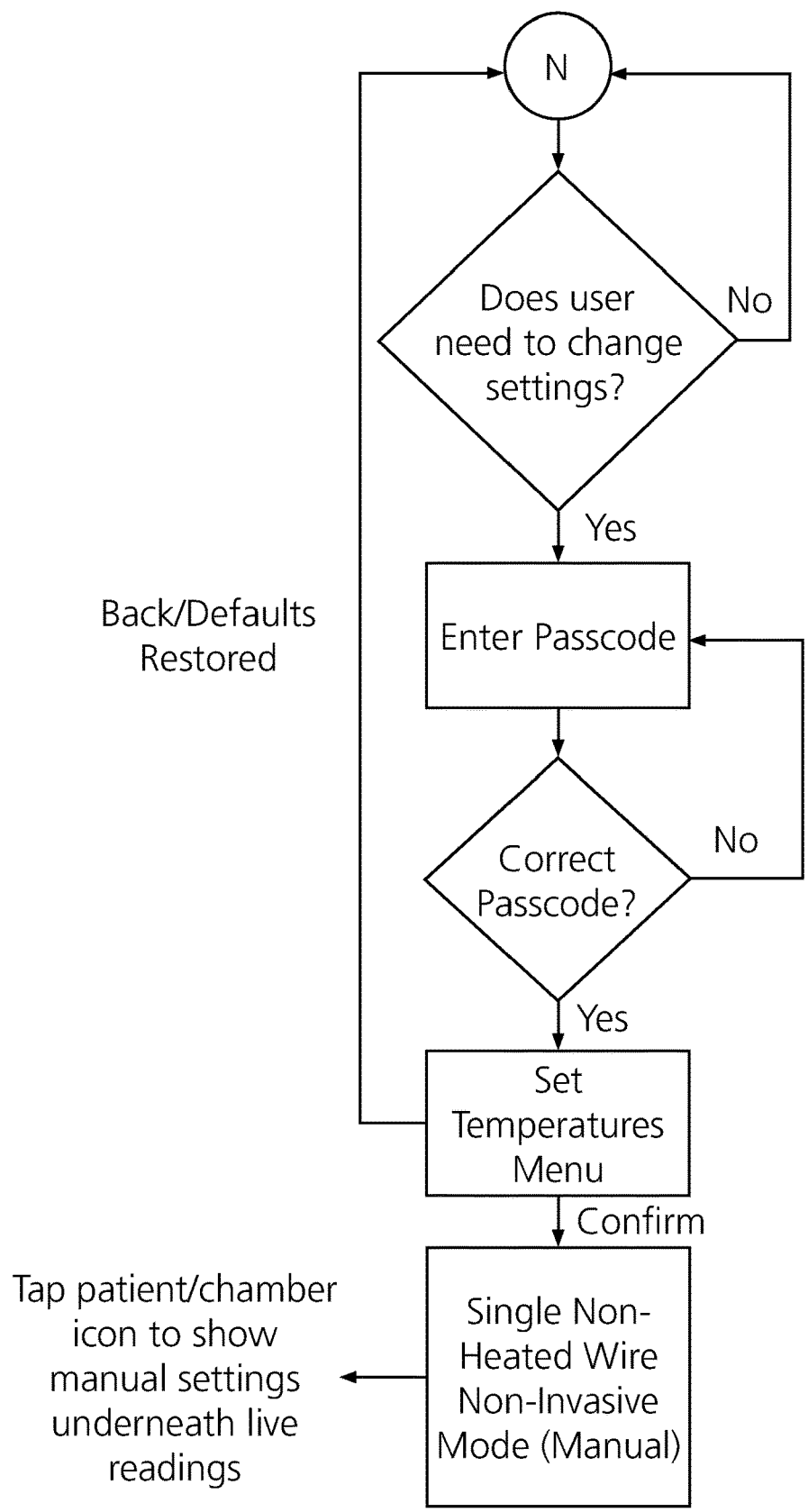
FIG. 21 is a flow diagram showing the operational screens for the user to amend the default settings for the mode selected in FIG. 11. Both the real-time measurements and settings can be simultaneously displayed.
Figure 22:
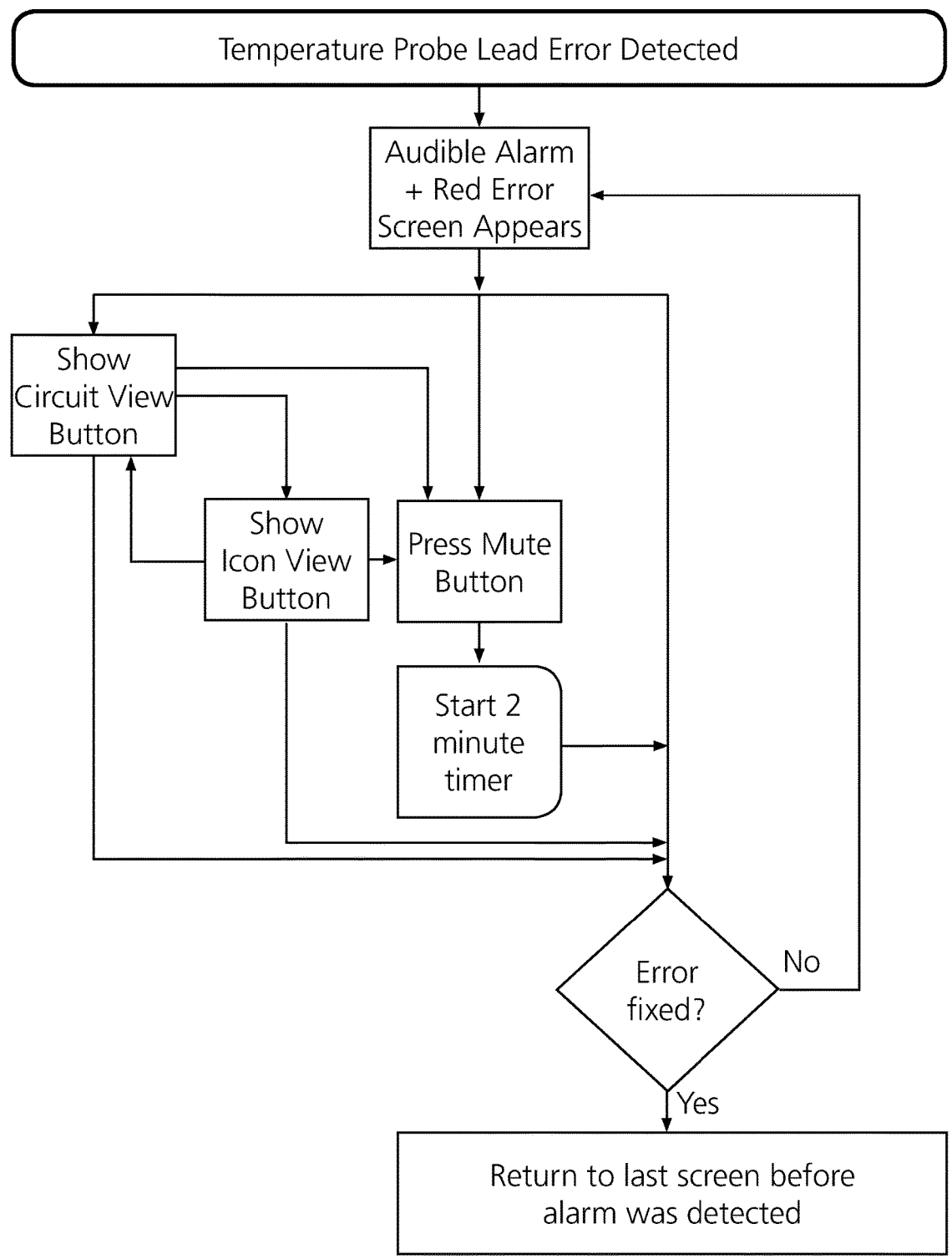
FIG. 22 is a flow diagram showing the operational screens for the visual indication of a detected fault and for the user to further investigate the source and mute any audible alarm.
Figure 23:
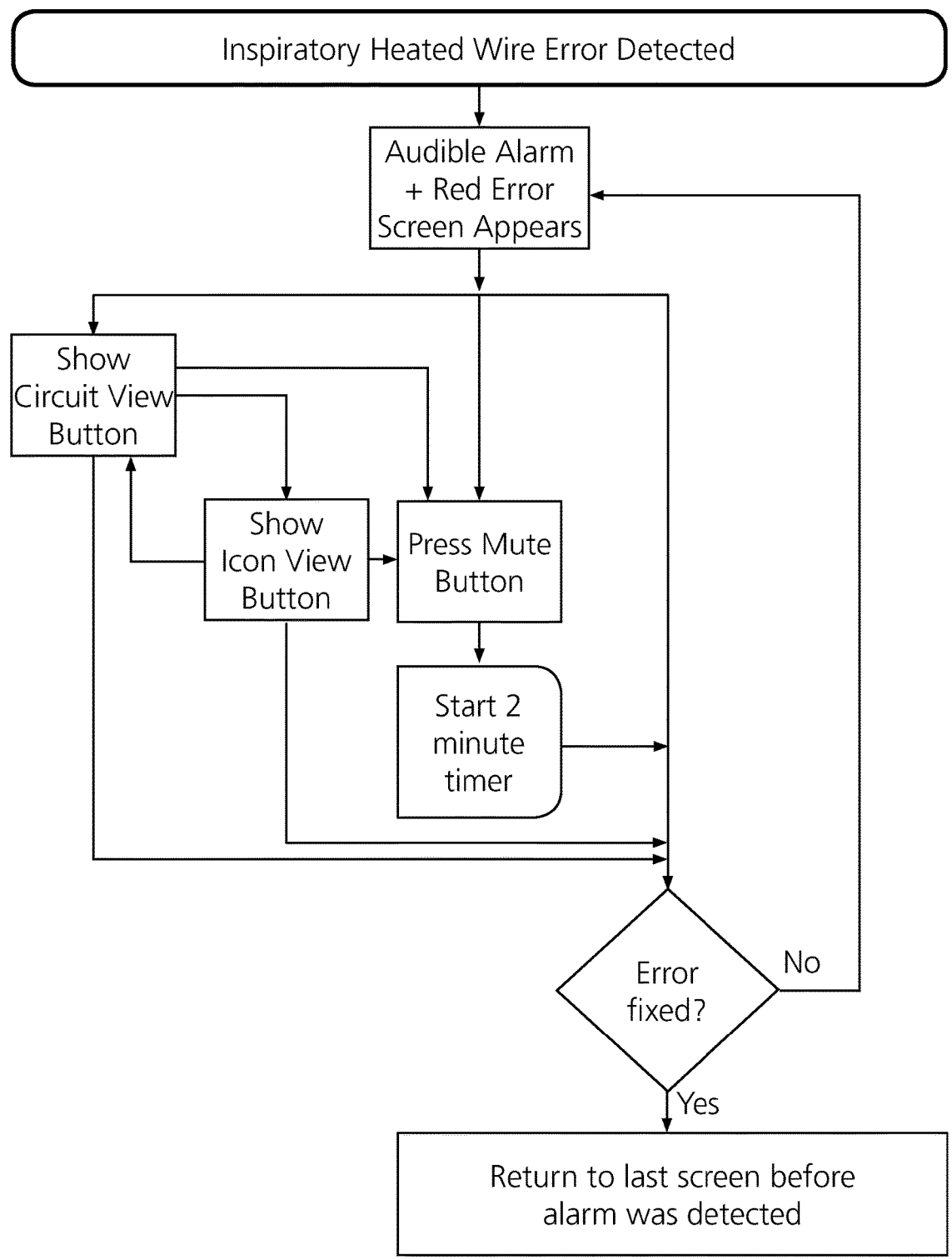
FIG. 23 is a flow diagram showing the operational screens for the visual indication of a detected fault and for the user to further investigate the source and mute any audible alarm.
Figure 24:
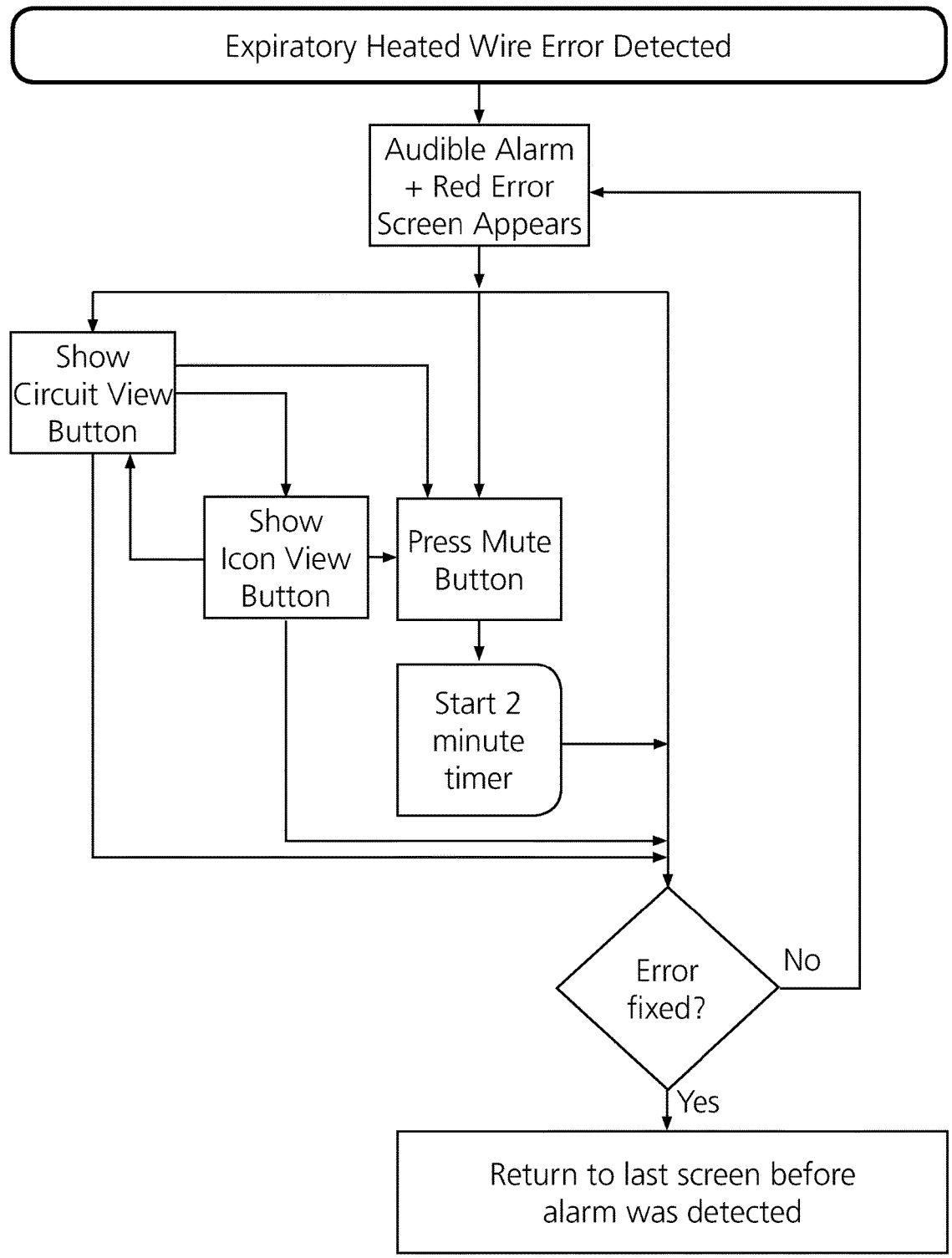
FIG. 24 is a flow diagram showing the operational screens for the visual indication of a detected fault and for the user to further investigate the source and mute any audible alarm
Figure 25:
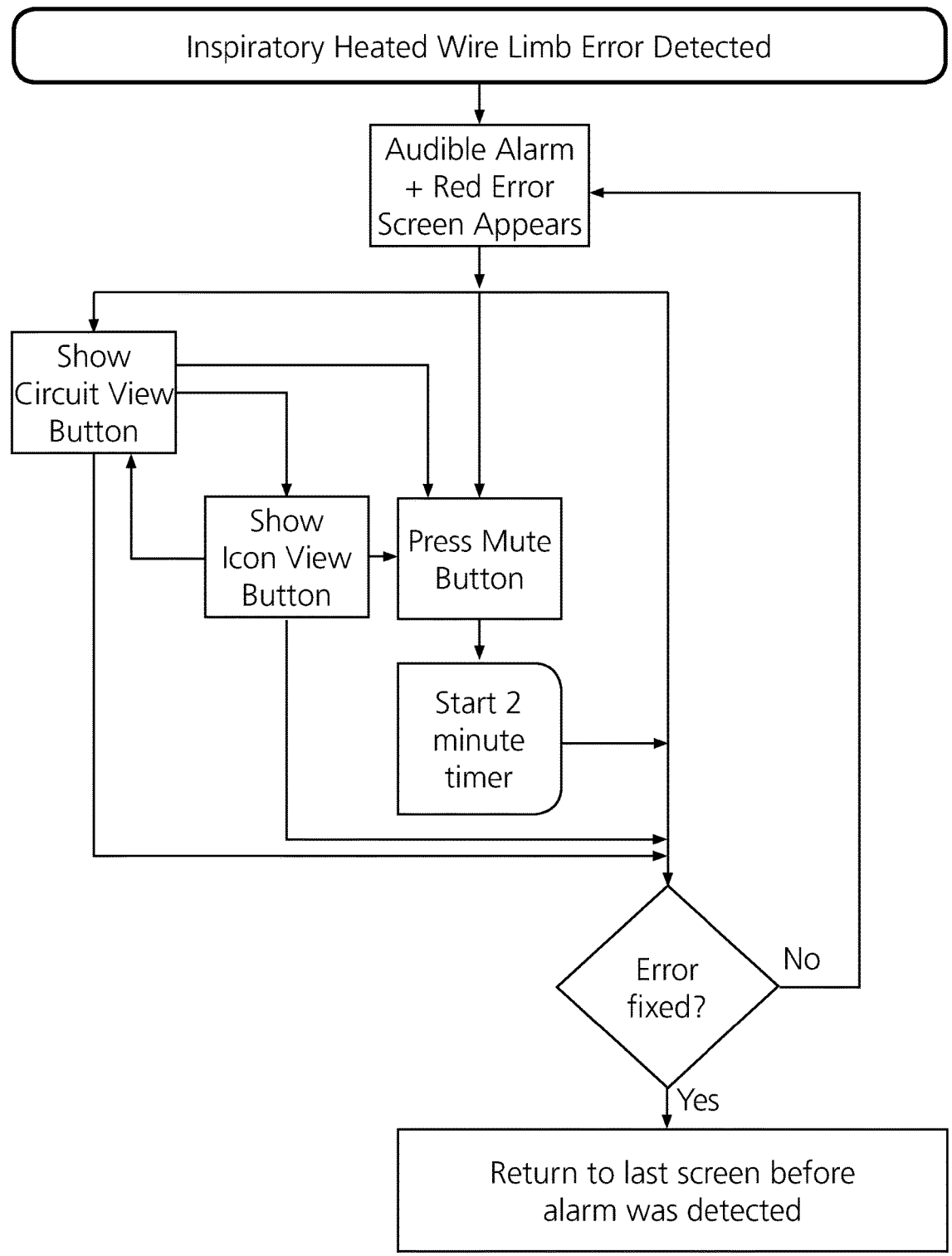
FIG. 25 is a flow diagram showing the operational screens for the visual indication of a detected fault and for the user to further investigate the source and mute any audible alarm.
Figure 26:
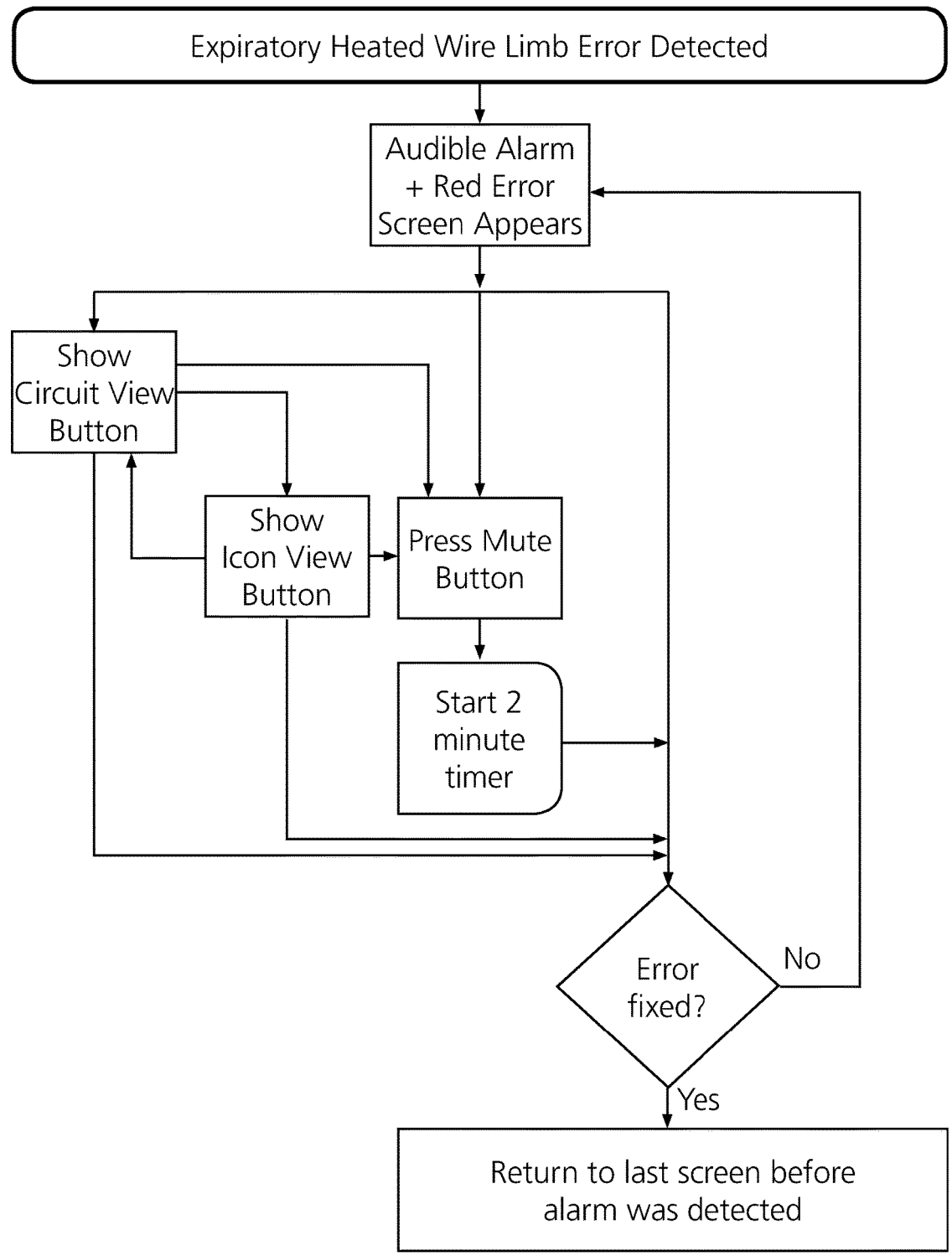
FIG. 26 is a flow diagram showing the operational screens for the visual indication of a detected fault and for the user to further investigate the source and mute any audible alarm.
Figure 27:
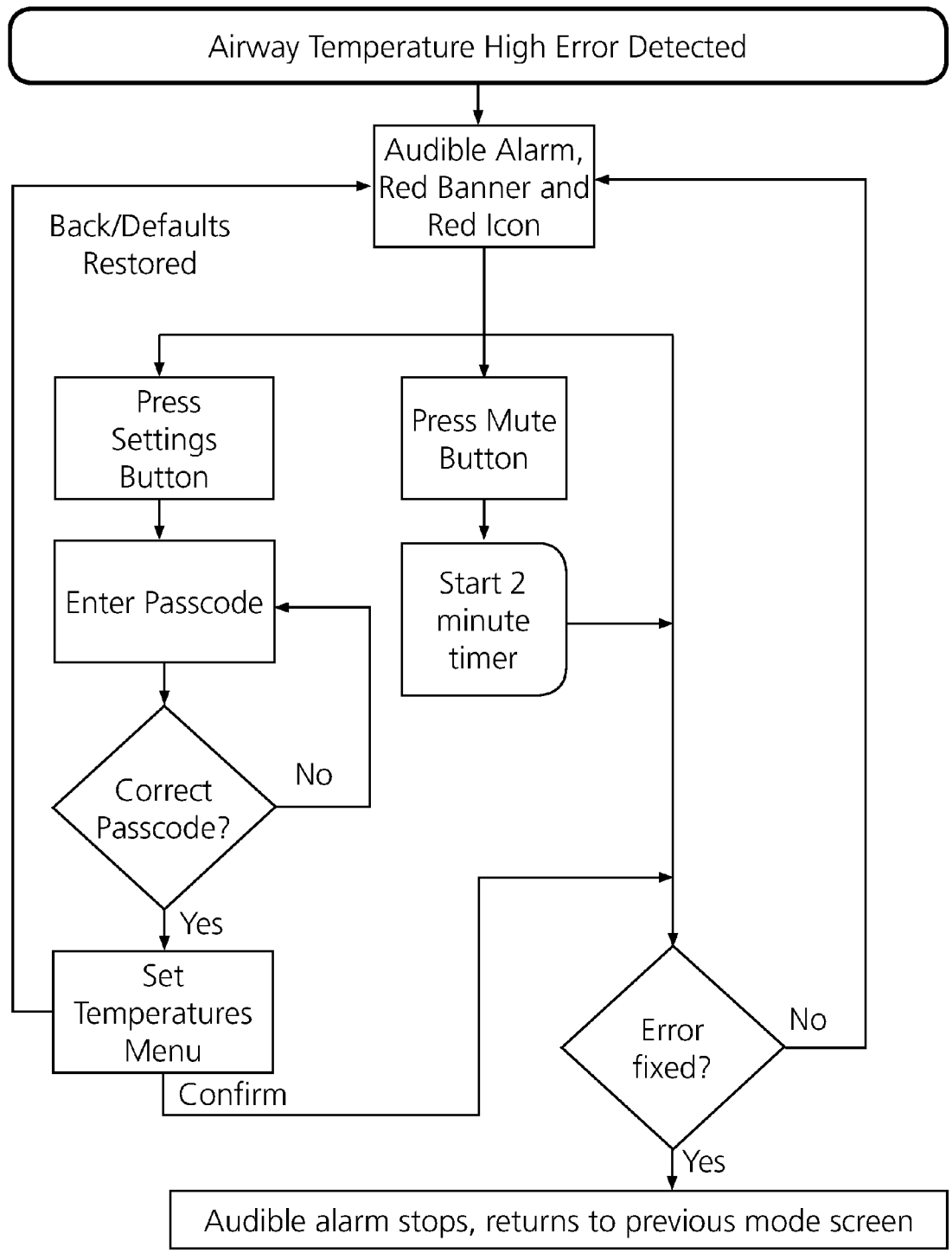
FIG. 27 is a flow diagram showing the operational screens for the visual indication of operation outside the set parameters and for the user to adjust settings and mute any audible alarm.
Figure 28:
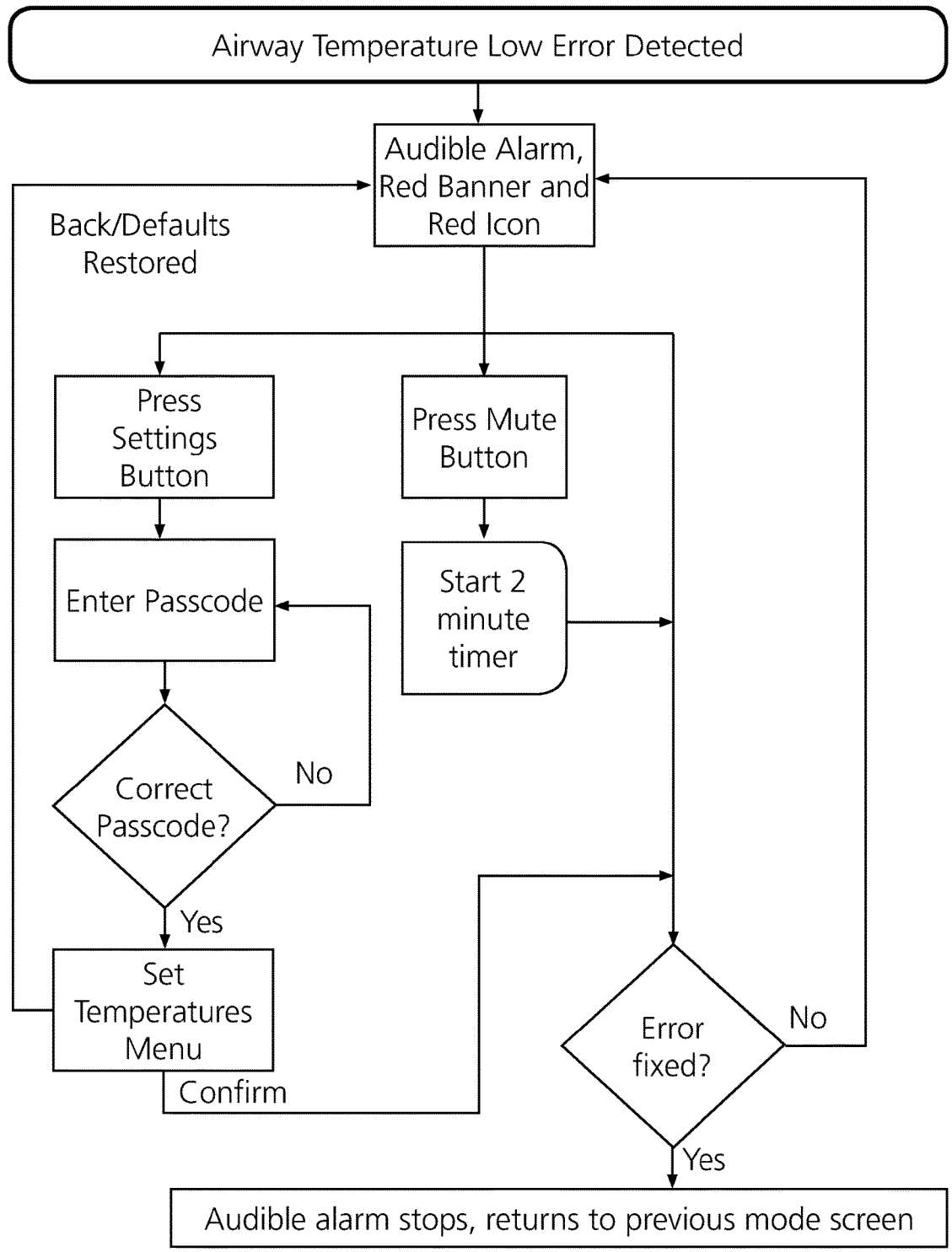
FIG. 28 is a flow diagram showing the operational screens for the visual indication of operation outside the set parameters and for the user to adjust settings and mute any audible alarm.
Figure 29:
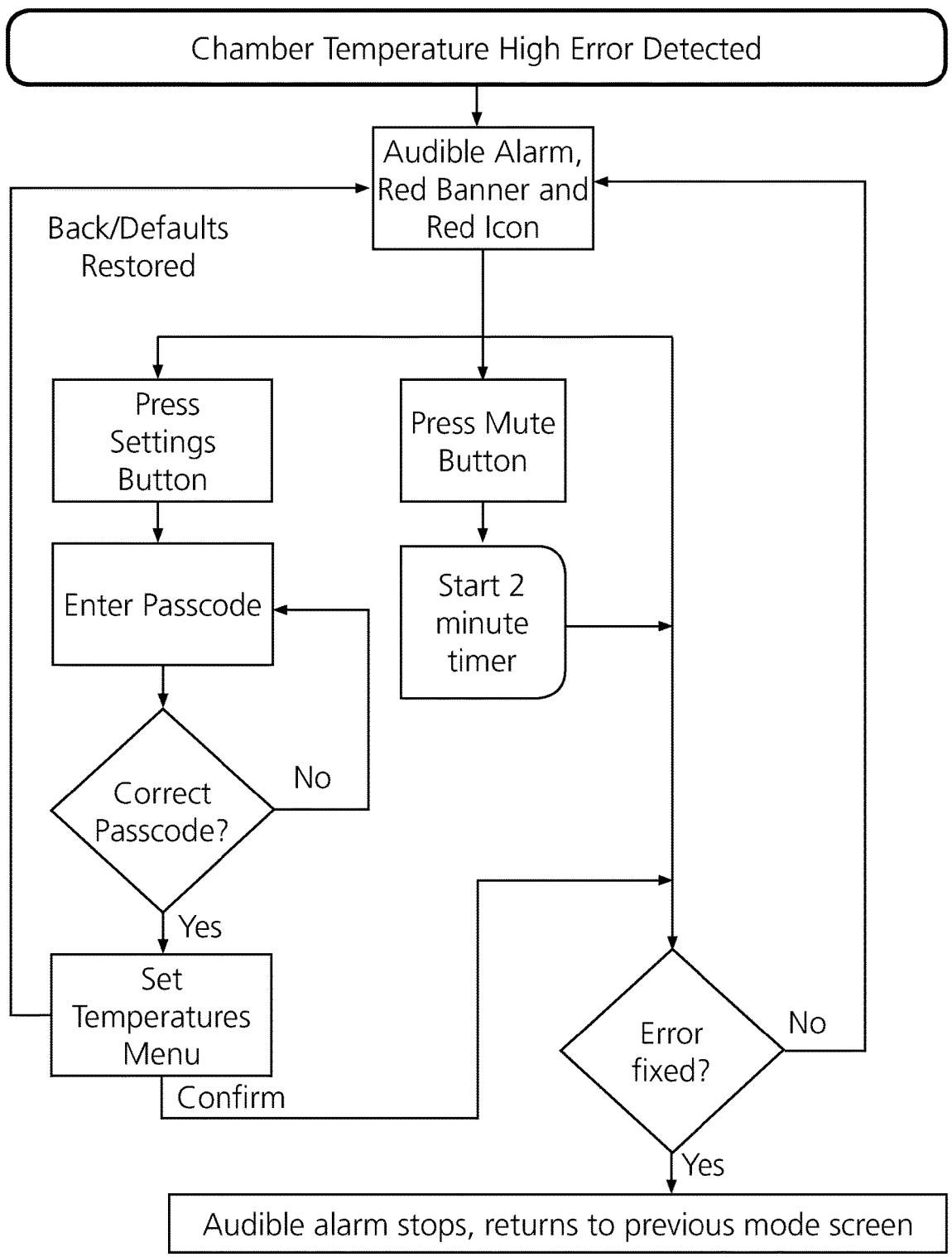
FIG. 29 is a flow diagram showing the operational screens for the visual indication of operation outside the set parameters and for the user to adjust settings and mute any audible alarm.
Figure 30:
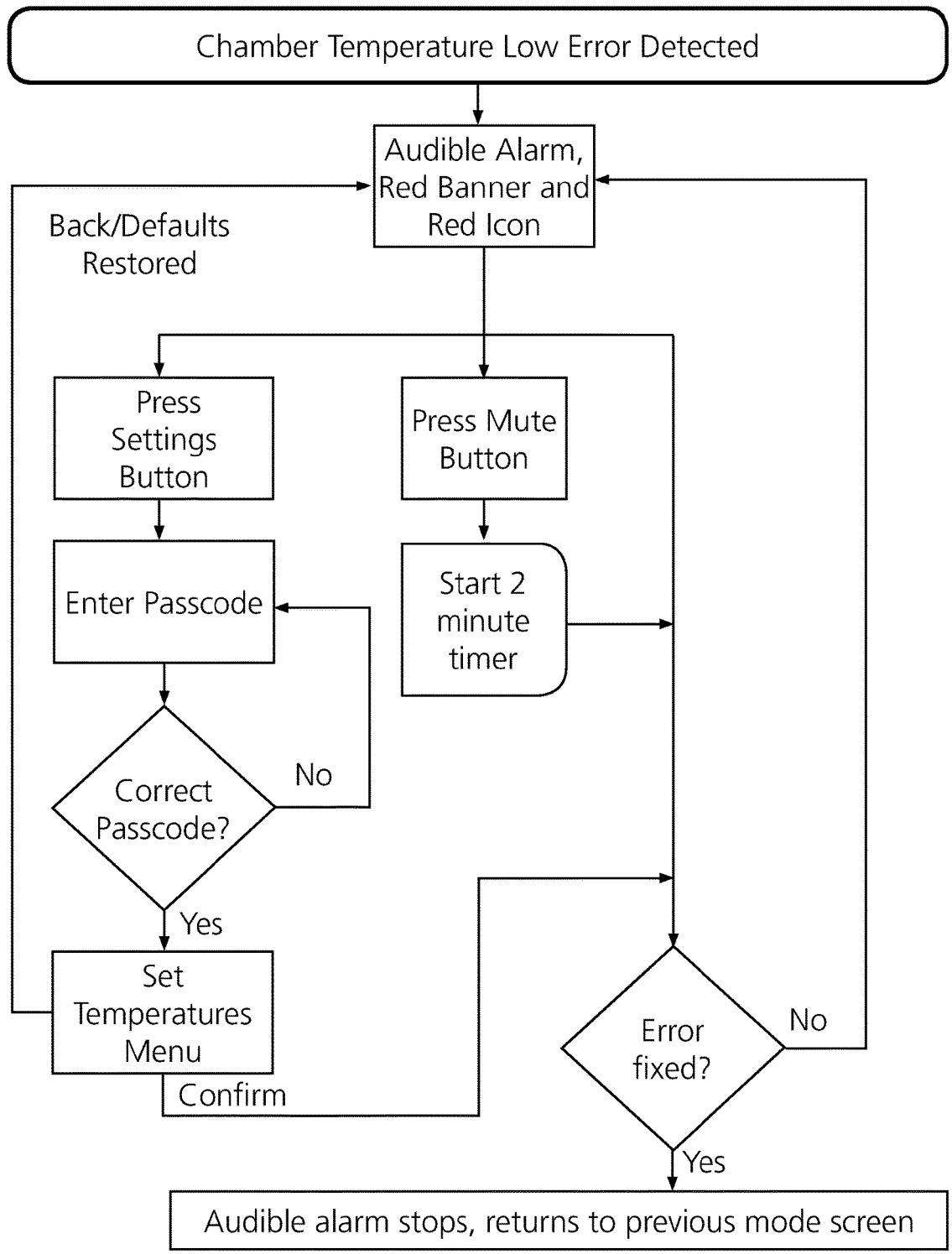
FIG. 30 is a flow diagram showing the operational screens for the visual indication of operation outside the set parameters and for the user to adjust settings and mute any audible alarm.
Figure 31:
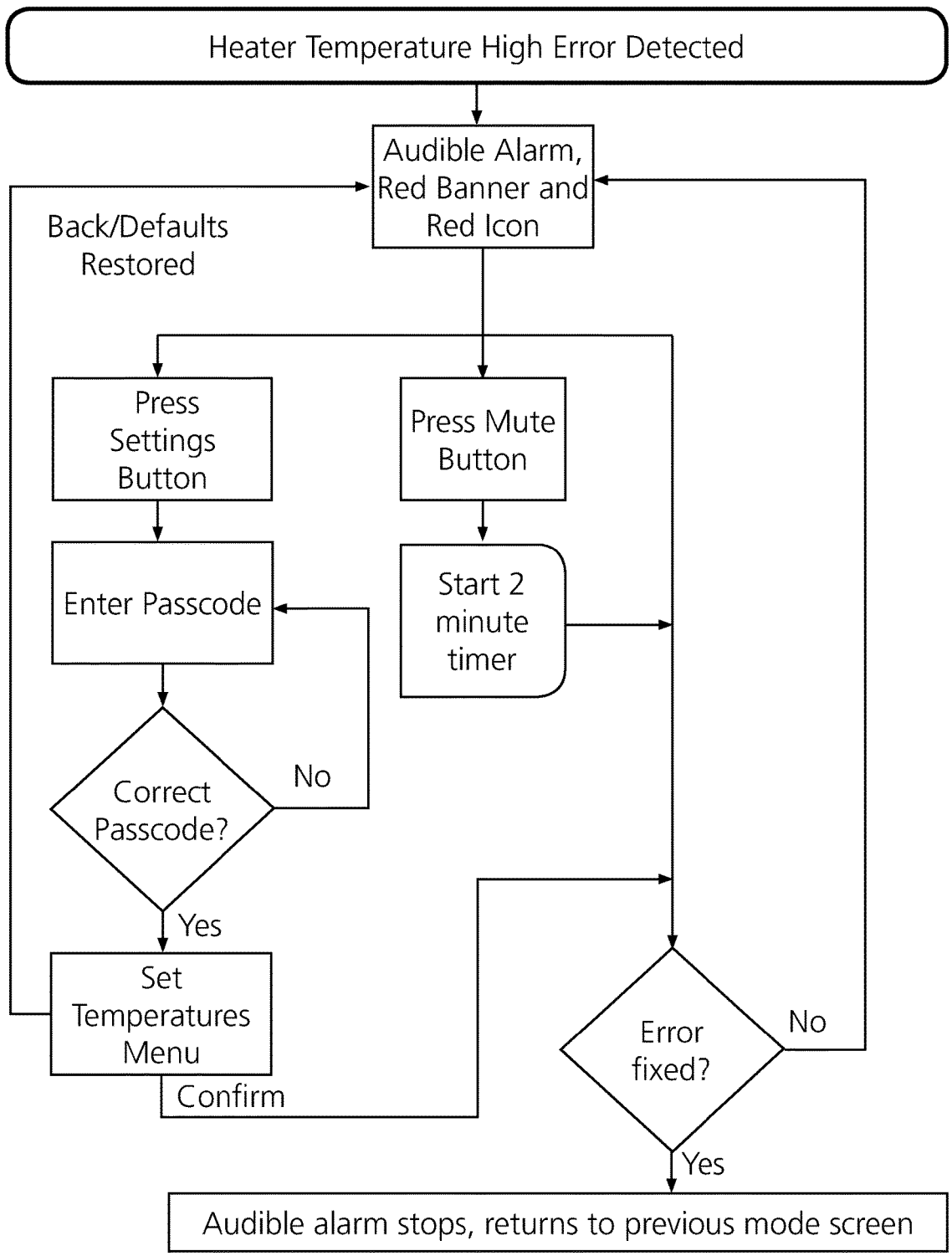
FIG. 31 is a flow diagram showing the operational screens for the visual indication of operation outside the set parameters and for the user to adjust settings and mute any audible alarm.
Figure 32:
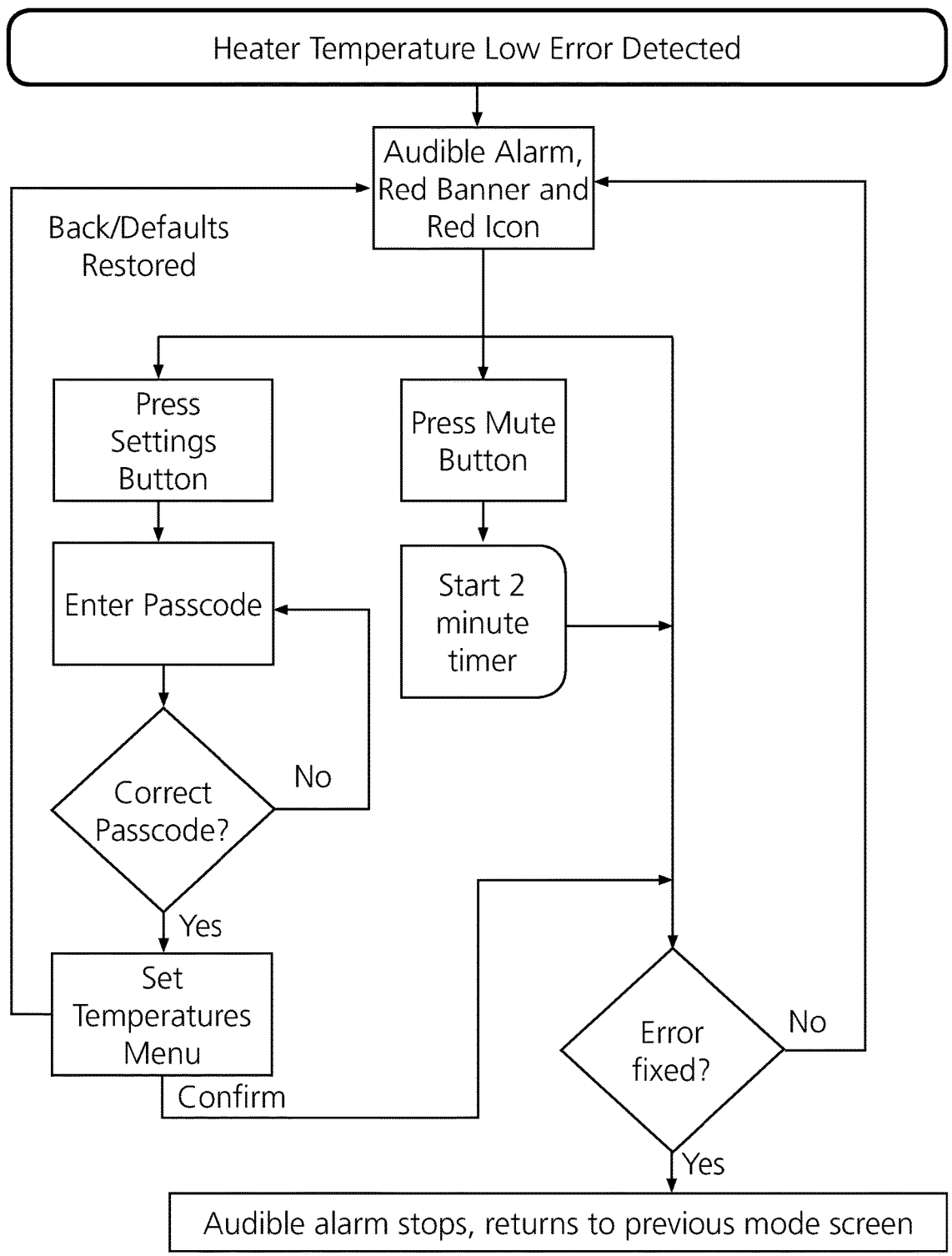
FIG. 32 is a flow diagram showing the operational screens for the visual indication of operation outside the set parameters and for the user to adjust settings and mute any audible alarm.
Figure 33:
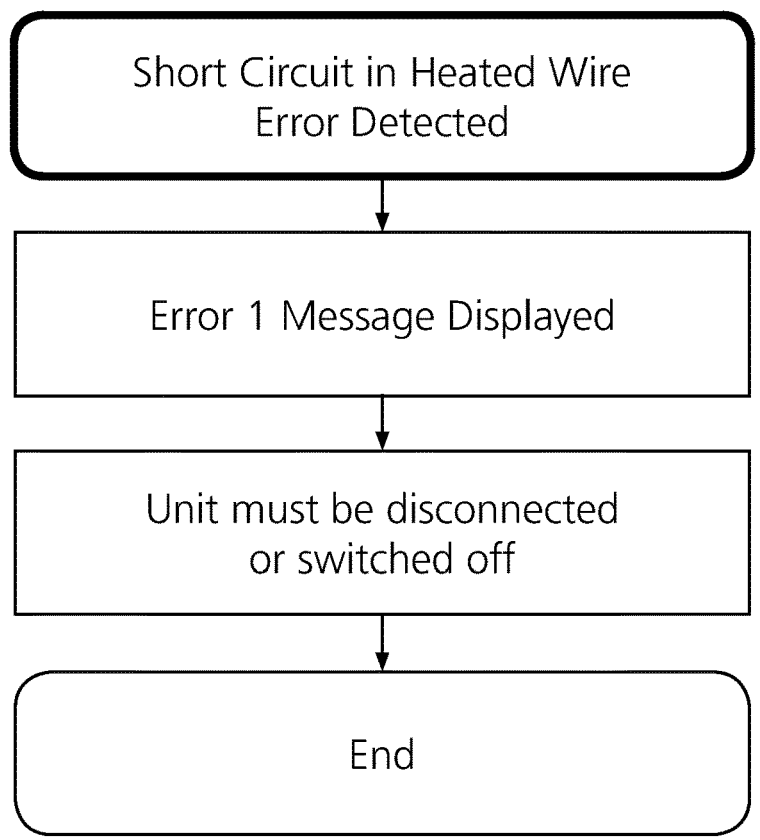
FIG. 33 is a flow diagram showing the information screens identifying a serious fault and prompting action by the user.
Figure 34:
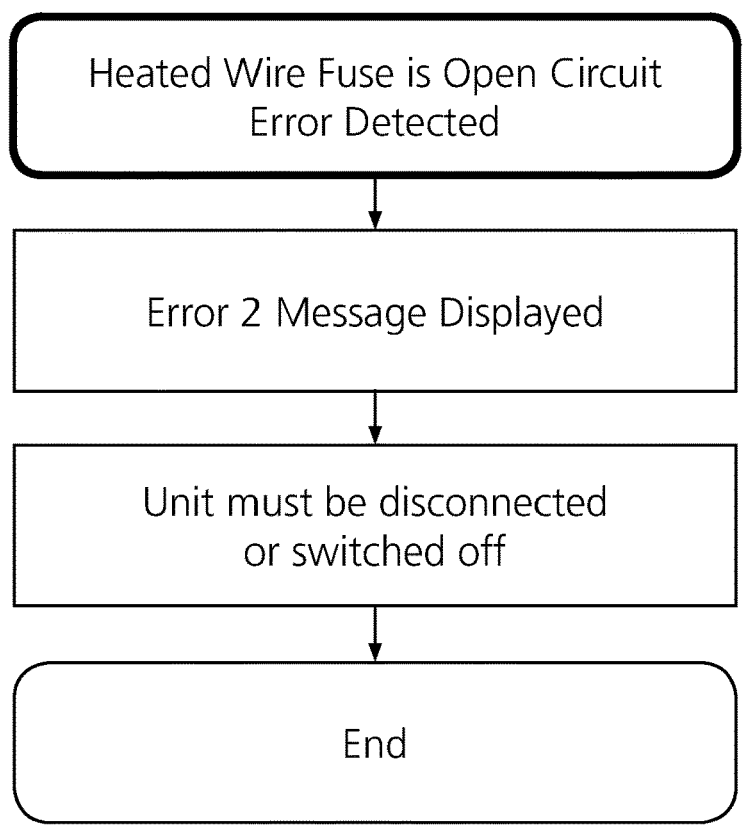
FIG. 34 is a flow diagram showing the information screens identifying a serious fault and prompting action by the user.
Figure 35:
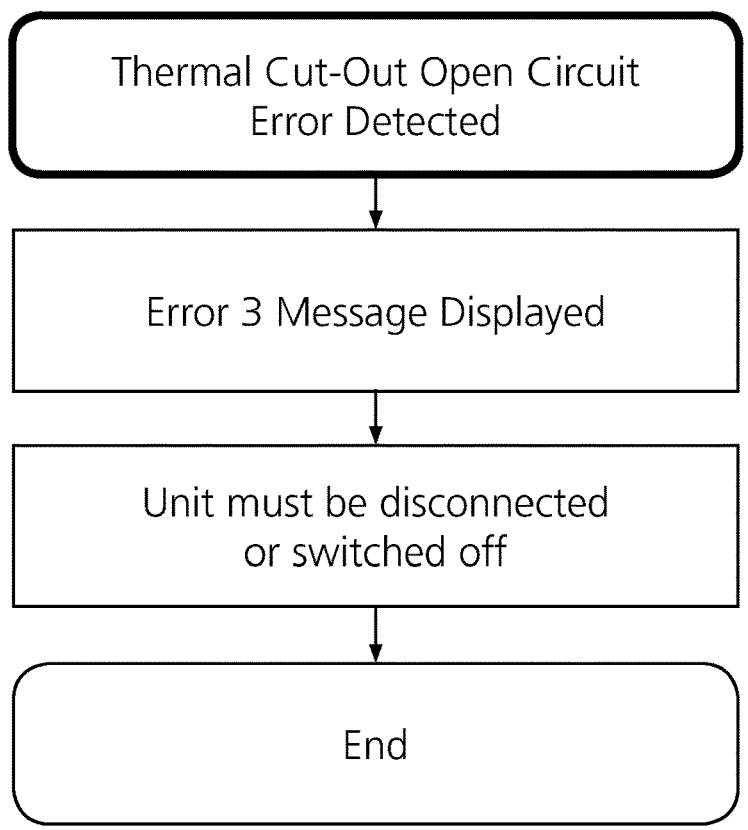
FIG. 35 is a flow diagram showing the information screens identifying a serious fault and prompting action by the user.

FIGS. 6 through 6B show the manner in which certain touch screen displays may vary from that described above if user initially selects to operate in non-heated wire/non-invasive mode. As shown in FIG. 6, the non-heated wire icon 14 and on-invasive icon 18 will illuminate when touched and, thereafter, a schematic system diagram 20n/n will appear as seen in FIG. 6A. This schematic system diagram screen 20n/n differs from that described above in relation to FIG. 5A only in that a non-invasive patient airway icon 28N appears instead of an invasive patient airway icon 28i. Also, if the user wishes to change a setting and enters a valid passcode which is accepted by the controller, a secure setting modification screen as shown in FIG. 6B will appear. This secure setting modification screen seen in FIG. 6B differs from that described above in relation to FIG. 5B only in that a non-invasive patient airway icon 62n appears in place of the invasive patient airway icon 62i. All other functions are the same as described above with respect to the heated wire/invasive mode of operation.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A system for delivering respiratory gas to a patient airway apparatus, said system comprising:
   a humidifier which has a heating element and a chamber having an outlet through which inspiratory gas or gas mixture flow out of the chamber;
   an inspiratory conduit having a chamber end connectable to the outlet of the humidifier chamber, a patient end connectable to the patient airway apparatus and a heating member extending along the inspiratory conduit for heating the inspiratory gas or gas mixture as it flows through the inspiratory conduit;
   an airway temperature sensor located at a patient airway sensor location at which the airway temperature sensor will sense an airway end temperature of the inspiratory gas or gas mixture when exiting the patient end of the inspiratory conduit after having been warmed by the heating member;
   chamber end temperature sensor located at a chamber end sensor location at which the chamber end temperature sensor will sense a chamber end temperature of the inspiratory gas or gas mixture when entering the chamber end of the inspiratory conduit prior to being warmed by the heating member; and
   a controller having a user interface configured to display a diagram of the system which includes:
   a) an indication of the chamber end sensor location as well as indications of i) said chamber end temperature as currently sensed by the chamber end temperature sensor and ii) a target chamber end temperature; and
   b) an indication of the patient airway sensor location as well as indications of said airway end temperature as currently sensed by the airway temperature sensor and a target airway end temperature;
   wherein the controller and user interface are further configured to initially assign and display default setting values for the target chamber end temperature and the target airway end temperature;
   wherein the controller and user interface are further configured to permit manual override of either or both of said default setting values by user input of override setting values that differ from the default setting values but are within predetermined acceptable ranges; and
   wherein the controller is programmed to control the humidifier heating element and the beating member of the inspiratory conduit to cause the sensed airway end temperature to be equal to or within a permissible range of the target airway end temperature setting and the sensed chamber end temperature to be equal to or within a permissible range of the target chamber end temperature setting.

2. A system according to claim 1 wherein the patient airway apparatus comprises either an invasive patient airway apparatus selected from endotracheal tubes, endobronchial tubes, nasotracheal tubes, tracheostomy tubes, supraglottic airways (SGA), laryngeal mask airways (LMA) and mouthpieces or a non-invasive patient airway apparatus selected from face masks, nasal masks, nasal cannulae, nasal plugs and breathing tents.

3. A system according to claim 1 wherein the user interface comprises a display.

4. A system according to claim 3 wherein the display comprises a touch screen display.

5. A system according to claim 1 wherein the diagram shows representations of the humidifier, inspiratory conduit, patient airway sensor location, and chamber sensor location.

6. A system according to claim 1 wherein the controller and user interface are further configured to display current airway humidity at the patient airway sensor location.

7. A system according to claim 6 wherein:
the controller and user interface are further configured to initially assign and display a default setting value for for target airway humidity;
the controller and user interface are further configured to permit manual override of said default setting value for the target airway humidity by manual input of an override setting value for target airway humidity within a predetermined acceptable range; and
the controller is further programmed to control the system to cause the current airway humidity to be equal to or within a permissible range of the target airway humidity setting value.

8. A system according to claim 7 wherein a passcode must be entered and accepted before user input of an override setting value for target airway humidity.

9. A system according to claim 7 wherein the user interface comprises a touch screen display.

10. A system according to claim 1 wherein the chamber end sensor location is within the humidifier chamber.

11. A system according to claim 1 wherein a passcode must be entered and accepted before user input of any override setting value.

12. A method for using the system of claim 1, said method comprising the steps of:
connecting the chamber end of the inspiratory conduit to the outlet of the humidifier;
connecting the patient end of the inspiratory conduit to the patient airway apparatus;
causing the system to deliver an inspiratory gas or gas mixture from the humidifier, through the inspiratory conduit and into the patient airway device while the controller controls the humidifier heating element and the heating member of the inspiratory conduit to cause the sensed airway end temperature to be equal to or within a permissible range of the target airway end temperature setting and the sensed chamber end temperature to be equal to or within a permissible range of the target chamber end temperature setting.

13. A system for heating and humidifying inspiratory gases in a patient ventilation circuit, said system comprising:
a) a humidifier which comprises a chamber and a humidifier heating element;
b) a gas heating element that is disposed or disposable on or in an inspiratory gas conduit which carries humidified inspiratory gas(es) from the humidifier to a patient;
c) temperature sensors for sensing temperature of inspiratory gas(es) at a first location that is either within the chamber or within a chamber end of the inspiratory conduit and a second location at a patient end of the inspiratory conduit so as to sense the temperature of the inspiratory as(es) flowing out of the inspiratory conduit to the patient after the inspiratory gas(es) has/have been heated by the gas heating element; and d) a controller configured to display a diagram showing the inspiratory as conduit, the first location and the second location, along with:
i) an indication of the current sensed temperature at the first location and a target first location temperature; and
ii) an indication of the current sensed temperature at the second second location and a target second location temperature;
wherein the controller is further configured to initially assign default setting values for said target first location temperature and said target second location temperature;
wherein the controller is further configured to permit a user to override the initially assigned default setting value for the target first location temperature by inputting an override setting value for the target first location temperature that is within a predetermined acceptable range, and to override the initially assigned default setting value for the target second location temperature by inputting an override setting value for the target second location temperature that is within L predetermined acceptable range; and
wherein the controller is further configured to control the system to cause the temperature sensed at the first location to be equal to or within a permissible range of the target first location temperature setting and the temperature sensed at the second location to be equal to or within a permissible range of the target second location target temperature setting.

14. A system according to claim 6 wherein the controller is further configured to:
display current airway humidity humidity of inspired gas(es) at the second location; and
initially assign a default setting value for target second location humidity;
permit a user to override the initially assigned default setting value for the target second location humidity by inputting an override setting value for the target second location humidity that is within a predetermined acceptable range;
wherein the controller is further configured to control the humidifier and heating element so as to cause the humidity sensed at the second location to be equal to or within a permissible range of the target second location humidity setting.

15. A system according to claim 13 wherein the controller has a touch screen display.

16. A system according to claim 15 wherein a user may use the touch screen display to view the diagram and to optionally enter one or more of said override setting values.

17. A system according to claim 13 wherein the controller is programmed to require entry of an acceptable passcode before allowing entry of any override setting value for the target first location temperature or any override setting value for the target second location temperature.

18. A system according to claim 14 wherein the controller is programmed to require entry of an acceptable passcode before allowing entry of an override setting value for the target second location humidity.

* * * * *